United States Patent [19]
Adams et al.

[11] Patent Number: 6,031,439
[45] Date of Patent: Feb. 29, 2000

[54] BI-DIRECTIONAL HALL-EFFECT CONTROL DEVICE

[75] Inventors: David V. Adams, San Carlos; Thomas G. Cooper, Menlo Park; Alan W. Petersen, Cupertino, all of Calif.; Karl Konecny, Hillsboro, Oreg.

[73] Assignee: Acuson Corporation, Mountain View, Calif.

[21] Appl. No.: 08/969,931

[22] Filed: Nov. 28, 1997

Related U.S. Application Data

[63] Continuation of application No. 08/553,062, Nov. 3, 1995, abandoned, which is a continuation-in-part of application No. 08/525,492, Sep. 8, 1995, abandoned.

[51] Int. Cl.$^7$ .................................................. H01H 9/00
[52] U.S. Cl. ............................................ 335/205; 335/207
[58] Field of Search .................. 335/205–7; 324/117 H, 324/126

[56] References Cited

U.S. PATENT DOCUMENTS

| | | | |
|---|---|---|---|
| 5,399,965 | 3/1995 | Heberle | 324/117 |
| 5,402,793 | 4/1995 | Gruner et al. | 128/660.1 |
| 5,413,107 | 5/1995 | Oakley et al. | 128/662.06 |
| 5,554,964 | 9/1996 | Jansseune | 335/207 |
| 5,578,977 | 11/1996 | Jansseune | 335/207 |
| 5,646,587 | 7/1997 | Miyazawa et al. | 335/207 |

*Primary Examiner*—Lincoln Donovan
*Attorney, Agent, or Firm*—Brinks Hofer Gilson & Lione

[57] ABSTRACT

A control device for converting a manual input into an electrical signal is provided. The control device includes a control button, a first magnet having a first predetermined polarity, a second magnet having a second predetermined polarity, and a hall-effect sensor located adjacent to the control button. The control button is mounted for pivotal displacement about a neutral position in accordance with the manual input. The first magnet and the second magnet are mounted to the control button. The polarity of the second magnet is opposite the polarity of the first magnet. The hall-effect sensor has an electrical input and an electrical output. The electrical signal produced by the control device may, for example, be used to control the velocity of a motor, which rotates an ultrasound transducer.

30 Claims, 15 Drawing Sheets

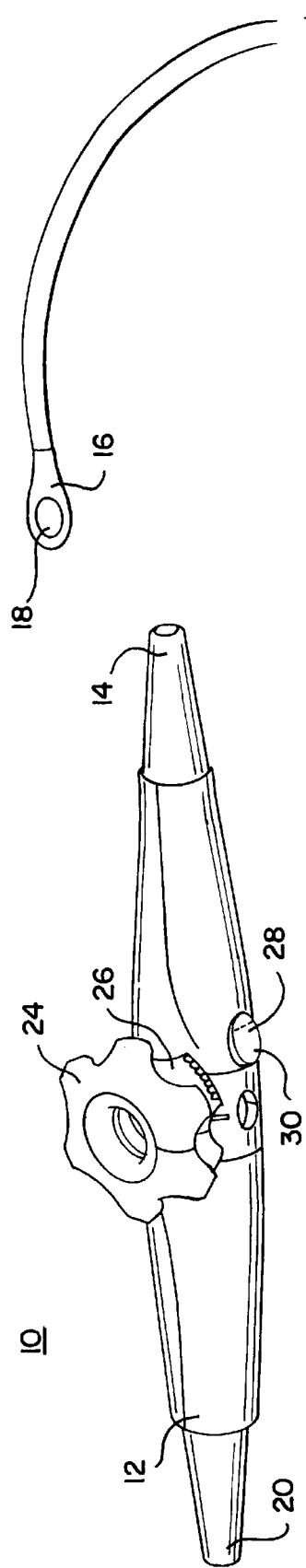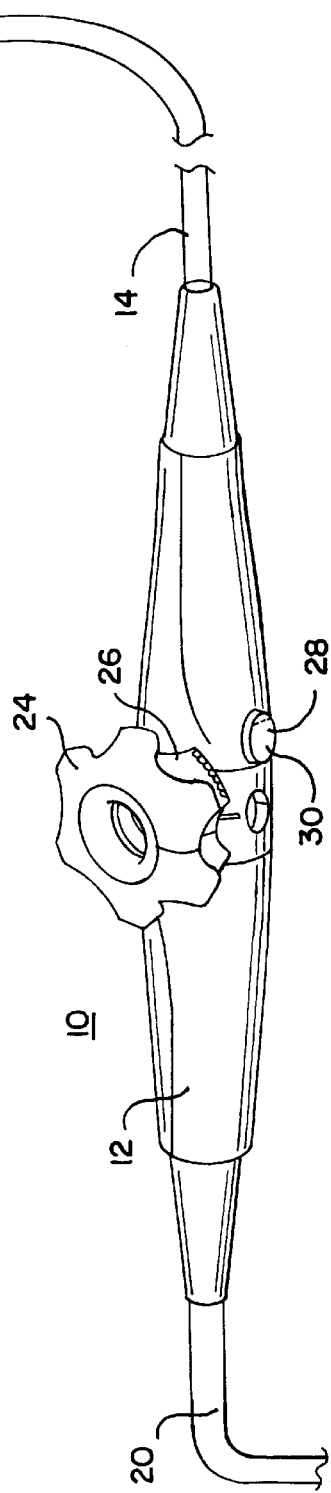
FIG. IA
FIG. IB

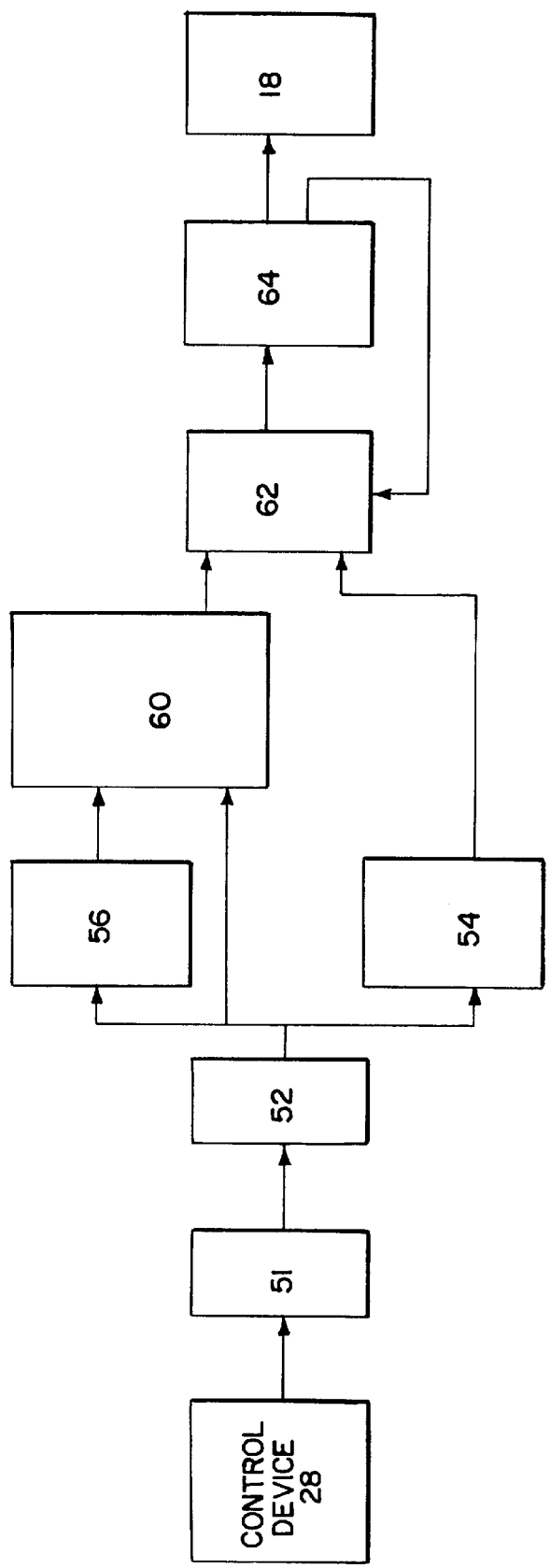

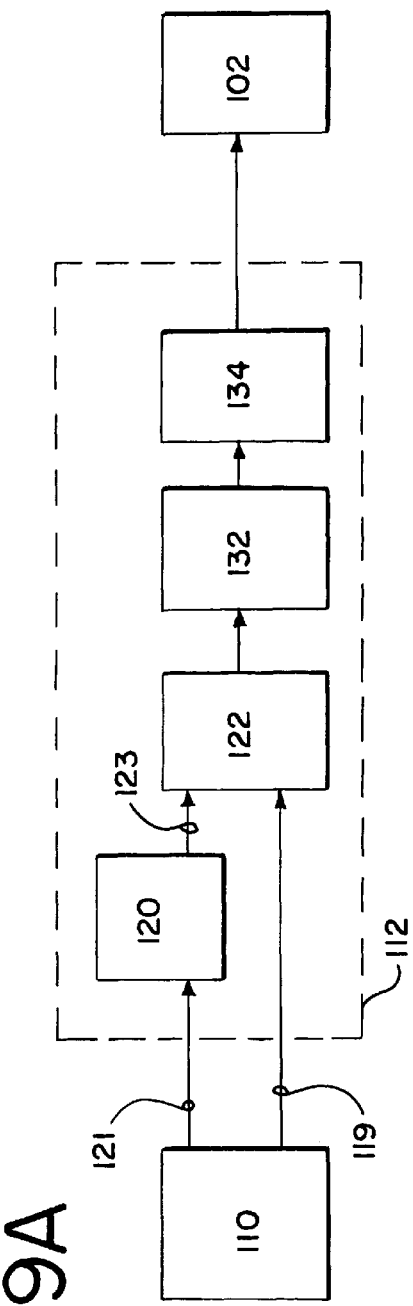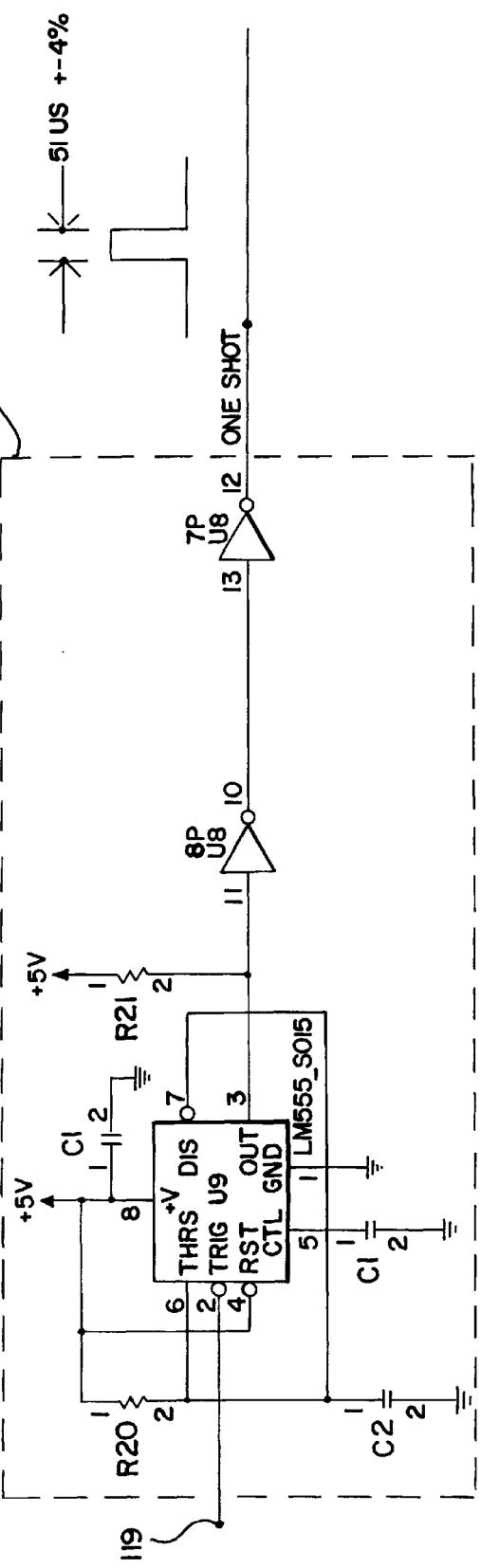
FIG. 9A
FIG. 9B

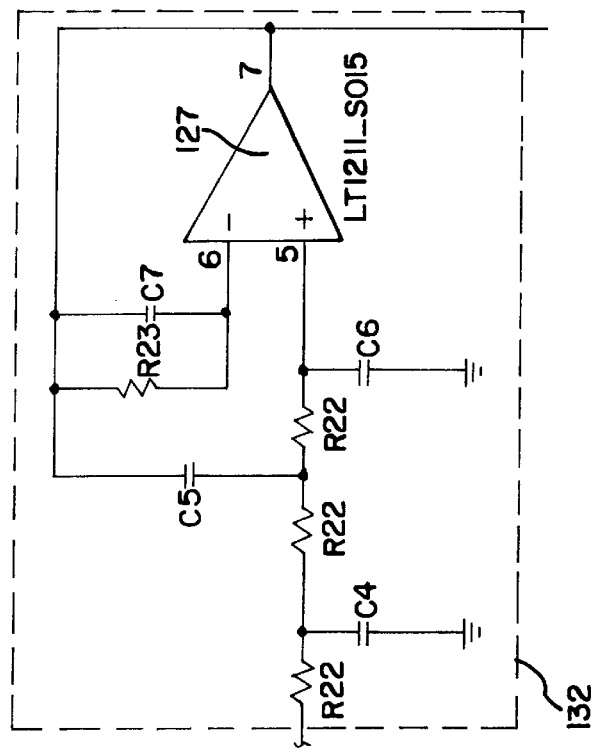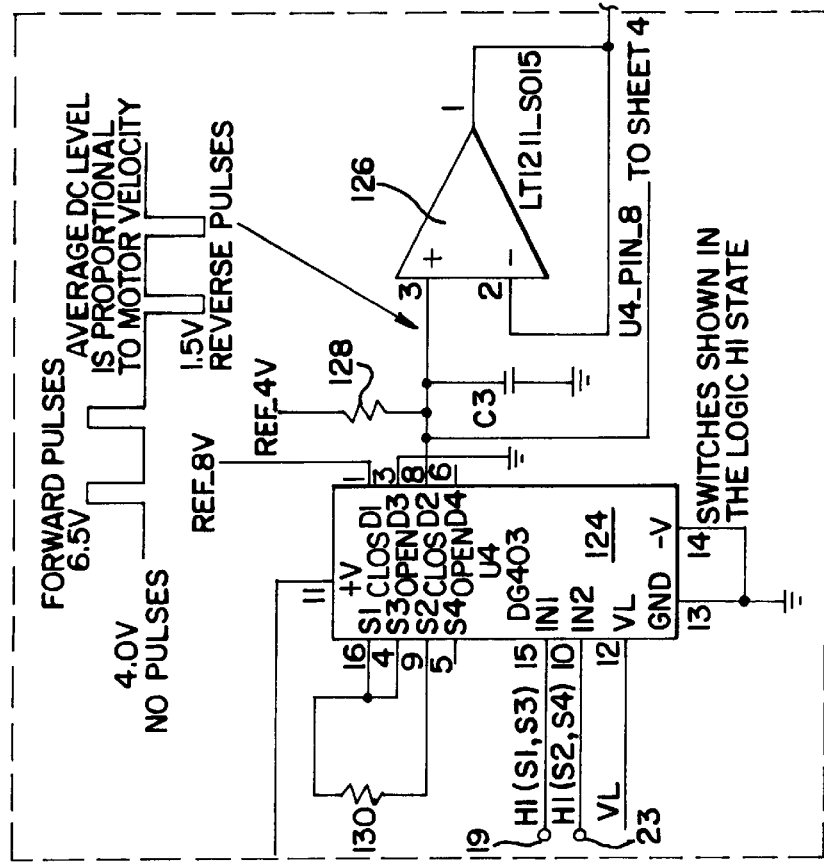

BI-DIRECTIONAL HALL-EFFECT CONTROL DEVICE

RELATED APPLICATIONS

This application is a continuation of application Ser. No. 08/553,062, filed Nov. 3, 1995, which is a continuation-in-part of U.S. patent application Ser. No. 08/525,492, filed on Sep. 8, 1995, now abandoned.

BACKGROUND OF THE INVENTION

The present invention relates to control devices and, more particularly, to a bi-directional hall-effect control device.

A control device, as the term is used herein, is a device that produces a desired effect in response to a manual input. In its simplest form, the handle of a tool is a control device. A light switch is slightly more complicated, but nonetheless clearly a control device. In applications where the control device is used frequently, it is desirable that the control device operate consistently and reliably.

In one application, control devices may be used in conjunction with medical ultrasound transducer probes. The users of medical ultrasound transducer probes, hereinafter referred to as sonographers, can obtain images of a region within a body by properly positioning a probe, using a control device such as a handle or knob, against the body. In order to obtain images having diagnostic value, the sonographer may have to physically manipulate the position of the probe by sliding, rotating and tilting the probe.

One area in particular where this manipulation is more challenging is transesophageal cardiac imaging. During transesophageal cardiac imaging, the sonographer positions a transducer housing at the tip of the probe against the esophagus or stomach of a patient to obtain different fields of view of the heart. For transesophageal cardiac imaging, the transducer housing typically contains a number of acoustic transducer elements, which may be sequentially electrically excited by an ultrasound control and operating system to obtain an image in an object plane that is perpendicular to the transducer housing and the transducer elements.

It has been found desirable to provide a control device to rotate the transducer elements contained within the transducer housing independently from the physical manipulation of the housing itself. In combination with the ability to slide, rotate and tilt the transducer housing, the ability to independently rotate the transducer elements within the housing gives the sonographer the ability to obtain an ultrasound image of any or all object planes orthogonal to the upper surface of the transducer elements at each location to which the housing can be moved.

Control devices that allow the sonographer to rotate the transducer elements independently from the transducer housing are known. For example, U.S. Pat. No. 5,402,793 to Gruner et al. shows an ultrasonic transesophageal probe for the imaging and diagnosis of multiple scan planes. The probe includes two buttons that respectively control the clockwise and counter-clockwise rotation of the transducer at the tip of the probe. Each of the buttons is a three-position switch: off, slow rotation and fast rotation. The states of the switches are transmitted to the ultrasound system, interpreted and converted to motor drive signals.

A disadvantage of the Gruner et al. device is that the sonographer is unable to utilize intermediate rotational speeds. A desired position may be overshot when the transducer is rotated in the fast mode, or may take too long to reach when the transducer is rotated in the slow mode. A further disadvantage of the Gruner et al. device is the added complexity, in manufacture and use, of requiring two switches to rotate the transducer. It is desirable to simplify the use and manufacture of the control device. In addition, it is desirable to allow the sonographer to quickly, easily and precisely control the rotational speed of the transducer.

Another known control device is a joystick. For many applications, however, the joystick is simply too large or cumbersome. It is desirable to minimize the size and weight of the control device. It is also desirable to provide a leak proof or hermetic seal around the control device so that the device may be cleaned, disinfected or used in humid environments.

Accordingly, it would be desirable to have an improved control device.

SUMMARY OF THE INVENTION

In accordance with a first aspect of the present invention, a control device is provided. The control device includes a pivot bracket, a control button mounted to pivot about the pivot bracket, means for generating a magnetic field, and means for sensing the magnetic field. The generating means is attached to the control button.

In accordance with a second aspect of the present invention, a control device for converting a manual input into an electrical signal is provided. The control device includes a control button, a first magnet having a first predetermined polarity, a second magnet having a second predetermined polarity, and a hall-effect sensor located adjacent to the control button. The control button is mounted for pivotal displacement about a neutral position in accordance with the manual input. The first magnet and the second magnet are mounted to the control button. The polarity of the second magnet is opposite the polarity of the first magnet. The hall-effect sensor has an electrical input and an electrical output.

The invention, together with its further objects and attendant advantages, will be understood by reference to the following detailed description taken in conjunction with the accompanying drawings.

BRIEF DESCRIPTION OF THE DRAWINGS

FIGS. 1A and 1B are perspective views of an ultrasound probe including a control device in accordance with the present invention.

FIG. 3 is a schematic for processing a signal generated by the control device shown in FIG. 2A to control rotation of an ultrasound transducer.

FIGS. 9A and 9B through 9F are a block diagram and an electrical schematics, respectively, of the velocity detector and velocity servo shown in FIG. 7A.

DETAILED DESCRIPTION OF THE PRESENTLY PREFERRED EMBODIMENTS

Figure 2A:
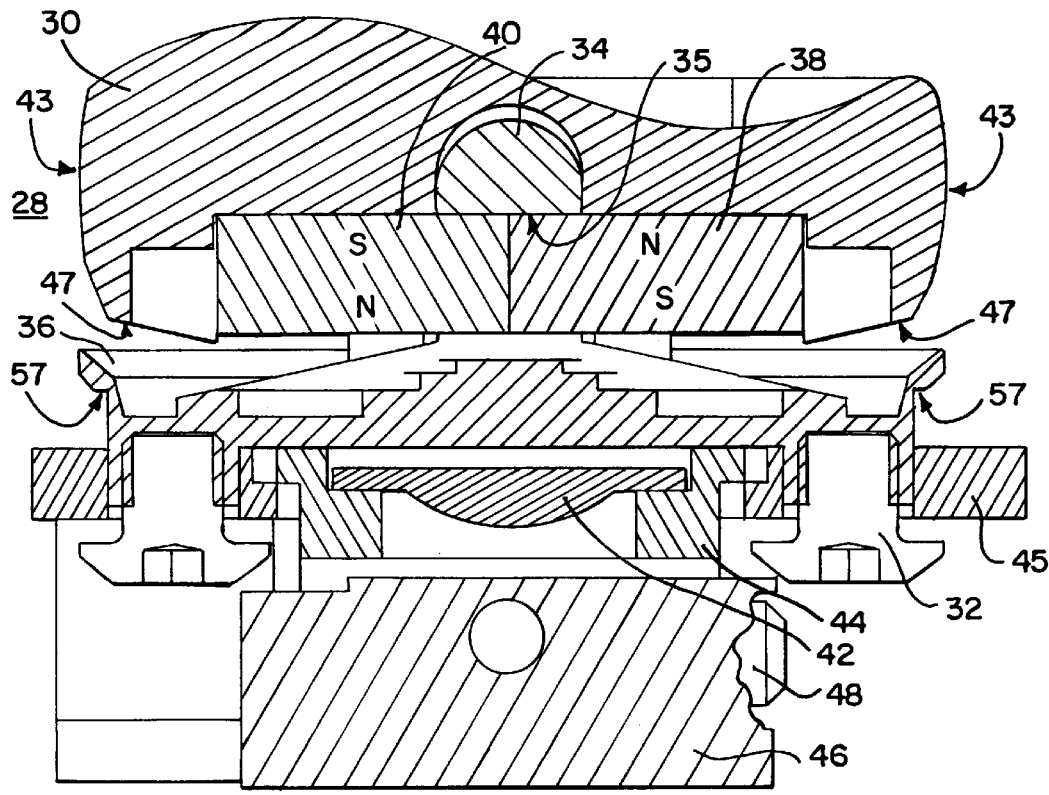
FIG. 2A is a sectional view of the control device mounted to the control housing of the ultrasound probe shown in FIGS. 1A and 1B, in which a control button of the control device is located in its neutral position.

The invention is described with reference to the drawings in which like elements are referred to by like numerals. FIGS. 1A and 1B are perspective views of an ultrasound probe 10 equipped with a control device 28 in accordance with the present invention. The ultrasound probe 10 has a control housing 12 which is designed to fit within the hand of the sonographer.

As shown in FIG. 1A, a gastroscope tube 14 connects the control housing 12 to a transducer housing 16. The transducer housing 16 contains an ultrasound transducer 18. An electrical cable 20 extends from the other end of the control housing 12 to a connector 22, which is designed to interface with an ultrasound control and operating system (not shown).

The control housing 12 contains the major manual controls that are used by the sonographer. The manual controls include control knobs 24 and 26, which are mechanically connected to the distal end of the gastroscope tube 14. As known within the art, the sonographer may cause left to right and forward to back articulation of the transducer housing 16 by rotating the control knobs 24 and 26, respectively. Thus, the control knobs 24 and 26 assist the sonographer in positioning the transducer housing 16 against the esophagus or stomach of a patient.

In accordance with the present invention, the control housing 12 also includes a control device 28, which may be manipulated by the sonographer to control rotation of the ultrasound transducer 18 within the transducer housing 16. Preferably, the ultrasound transducer 18 is mounted within the transducer housing 16 to rotate between a 0° position, also referred to herein as the home position, and a 180° position. It will be recognized that rotation of the two-dimensional image plane through 180° provides a full 360° of scanning coverage.

As shown in FIGS. 1A and 1B, the control device 28 is preferably operated by a control button 30 that is located on the control housing 12 in a position where it typically may be operated by the sonographer's thumb or finger. In FIGS. 1A and 2A, the control button 30 is shown in its neutral position, whereas the control button 30, as shown in FIG. 1B, is fully tilted in the forward direction.

FIG. 2A is a sectional view of a preferred embodiment of the control device 28 shown in FIGS. 1A and 1B. The control device 28 includes the control button 30, which is mounted about a pin 34 on a pivot bracket 36 so that the control button 30 may tilt back and forth about its neutral or balanced position on the pivot bracket 36.

The travel limits for the tilting movement of the control button 30 may be defined by the pivot bracket 36. In particular, the control button 30 may be tilted back or forth upon the pivot bracket 36 until the contact surfaces 47 of the control button 30 strike the pivot bracket 36, as shown in FIGS. 2E and 2F.

As shown in FIG. 2A, two magnets 38 and 40 are attached to the lower surface of the control button 30. The magnets 38 and 40 are oriented so that their north poles face in opposite directions and their faces are parallel. The first magnet 38 is oriented with its north pole facing upward while the second magnet 40 is oriented with its north pole facing downward.

Figure 2B:
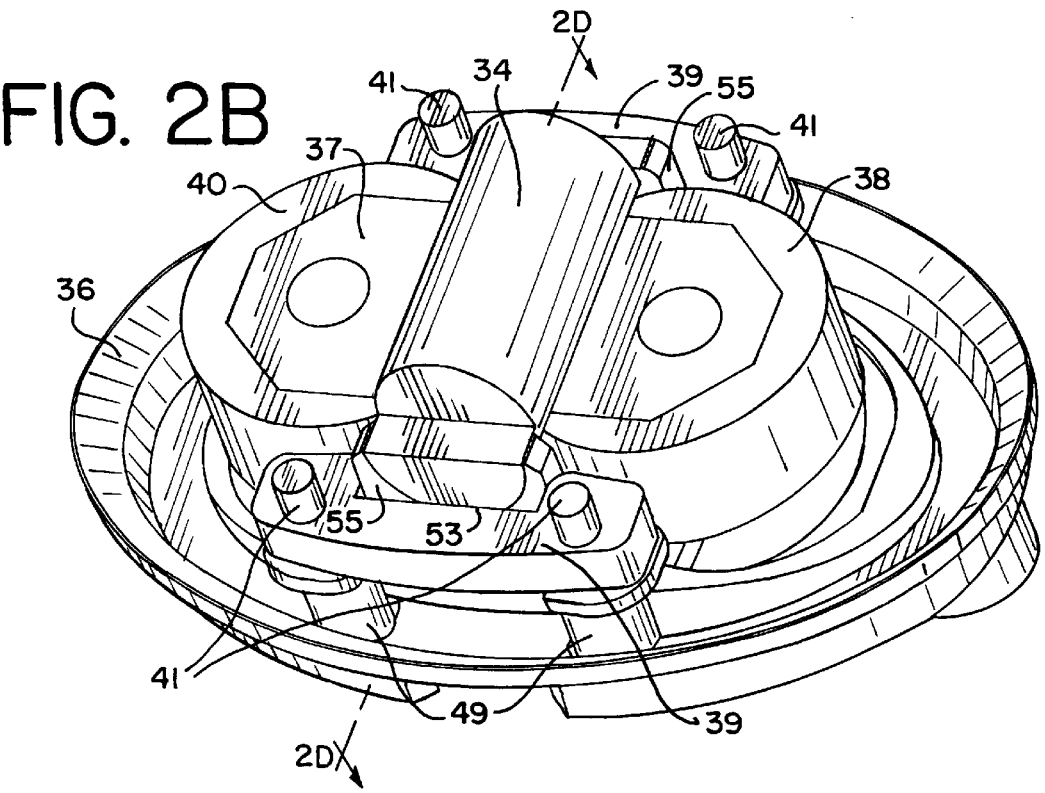
FIG. 2B is an isometric view of a portion of the control device shown in FIG. 2A showing a pair of return springs.

As noted above, the magnets 38 and 40 are located in the control device 28 so that their faces are parallel and their polarities are opposite, as shown in FIGS. 2A and 2B. Because the magnets 38 and 40 are opposite in polarity, there exists a plane bisecting the magnets 38 and 40 in which the magnetic field decreases to zero gauss. When the control button 30 is in the neutral position, the zero-gauss plane passes through the hall-effect sensor 42.

A hall-effect sensor 42 is positioned within the control housing 12 below the pivot points of the control button 30, as shown in FIG. 2A. Preferably, the hall-effect sensor 42 is mounted within the control housing 12 so that its position may be adjusted. The hall-effect sensor 42 is preferably adjustably mounted because it is difficult to obtain magnets 38 and 40 that have precisely the same strength. The position of the hall-effect sensor 42 may therefore need to be adjusted so that the magnetic field null plane between the oppositely oriented magnets 38 and 40 intersects the hall-effect sensor 42 when the control button 30 is in the neutral position.

As shown in FIG. 2A, the hall-effect sensor 42, for example, may be mounted upon an adjustable bracket 44. The bracket 44 is attached to a clamp plate 45 by an adjusting screw 48. The bracket 44 is formed from a non-ferromagnetic material, such as polyethylene terephthalate ("PET"). PET is commercially available from Erta, Inc. of Exton, Pa. under the tradename ERTALYTE. A spring 50 (not shown) is positioned around the adjusting screw 48 between the clamp plate 45 and the bracket 44. The position of the hall-effect sensor 42 may be adjusted by using the adjusting screw 48 to slide the bracket 44 with respect to the pivot bracket 36 and a clamp plate 45.

A hall shoe 46 is preferably attached to either the clamp plate 45 or the bracket 44. Preferably, the hall shoe 46 is formed from a ferromagnetic material, such as steel. The hall shoe 46 is a rectangular bar that functions to concentrate the magnetic field in the vicinity of the hall-effect sensor 42. The hall shoe 46 may be attached using, for example, a screw(s) or an adhesive. The hall shoe 46 may alternatively be mounted to an inner surface of the control housing 12. Alternative schemes for adjustably mounting the hall-effect sensor 42 will be apparent to those of ordinary skill in the art.

Referring again to FIG. 2A, the bracket 44 is supported by the clamp plate 45. The clamp plate 45 is secured to the pivot bracket 36 by a fastener 32, such as a screw. By securing the clamp plate 45 to the pivot bracket 36, the fastener 32 prevents relative motion between the hall-effect sensor 42 and the magnets 38 and 40, except as may be provided by the adjusting screw 48. While only one fastener 32 is required to secure the clamp plate 45 to the pivot bracket 36, two fasteners 32 may optionally be used, as shown in FIG. 2A. The clamp plate 45 is preferably formed from aluminum, a non-ferromagnetic material.

The balanced or central position of the control button 30, as shown in FIGS. 1A and 2A, is referred to herein as the neutral position. When the control button 30 is in the neutral position, the magnets 38 and 40 lie adjacent to a flat surface 35 of the pivot pin 34. Preferably, a shim 37 is located between the magnets 38 and 40 and the pivot pin 34, as shown in FIG. 2B. The surface 35, alternatively, may be concave.

FIG. 2B is an isometric view of the control device 28 in which the control button 30 has been omitted for clarity. The shim 37 reduces particulate formation that may otherwise occur if the magnets 38 and 40 were to contact the pivot pin 34 during use of the control device 28. The shim 37 is preferably formed from 0.002" thick austenitic (300 series) stainless steel. The shim 37 alternatively may be formed from other materials, although wear and corrosion-resistant materials are preferred, or it may be omitted entirely. If the shim 37 is omitted entirely, however, the useful life of the control device 28 may be decreased.

As shown in FIG. 2B, the magnets 38 and 40 are round disk magnets having a diameter of approximately 0.25 inches and a thickness of 0.100 inches. The magnets 38 and 40 are magnetized parallel to their thickness. A preferable magnet material is Samarium-Cobalt 26, which is resistant to corrosion and demagnetization and provides a fairly strong magnetic field relative to its size. A commercially available magnet that is suitable for this application is available from Dexter-Magnetic Materials Division in Fremont, Calif. as part no. 30808. Magnetic field strength may vary from magnet to magnet in typical commercially available magnets. In addition, magnets typically have a strong pole, which exhibits a stronger magnetic field, and a weak pole. Accordingly, the magnets are preferably sorted for use in the control device 28 so that a magnet having a strong north pole is paired with a magnet having a strong south pole. In addition, the strong pole of a given magnet is preferably oriented toward the hall-effect sensor 42.

It is preferable that the magnets have sufficient magnetic field strength to saturate the hall-effect sensor 42 when the control button 30 is fully displaced in both the forward and reverse directions. In this manner, the entire range of signal variation available from the hall-effect sensor 42 is utilized.

Other magnet materials, sizes and shapes, such as square, D-shaped or hexagonal, may alternatively be used. However, for applications in which the size and weight of the control device 28 are to be minimized, such as the ultrasound transducer probe 10 described herein, magnets having the approximate size of and providing equivalent magnetic field strength to the Dexter 30808 magnets are preferred. For applications in which larger size control devices may be tolerated, larger magnets, which generally produce a stronger magnetic field for a given magnetic material, may be used, or the travel range of the magnets may be increased to bring the magnets in closer proximity to the hall-effect sensor at the travel limits.

Preferably, the control button 30 is biased to return to its neutral position when manual pressure is removed from the control button 30. In this manner, the sonographer may stop rotation of the ultrasound transducer 18 by simply releasing the control button 30. The control button 30 may be biased to return to its neutral position by positioning two return springs 39, as shown in FIG. 2B, between the control button 30 (not shown for clarity) and the pivot bracket 36. The return springs 39 are symmetrically constructed and positioned to respond in the same manner to displacements in either the forward or reverse directions.

The return springs 39 are preferably formed by casting an elastomer, such as silicone rubber. Silicone rubber is a non-magnetic elastomer that is capable of sustaining a large number of bending and flexing cycles without damage. A silicone rubber that is suitable for this application is made by Dow-Corning of Midland, Mich. as RTV part no. Q5-8008. As an alternative to Dow-Corning RTV Q5-8008, the return springs may be formed from any commercially available silicone rubber having a durometer rating of Shore A 56±10.

As shown in FIG. 2B, the return springs 39 each have two cylindrical projections 41, which may be used to secure the return springs to the underside of the control button 30. In addition, each of the return springs 39 has a pair of feet 49 extending toward a recess in the pivot bracket 36. A C-shaped recess 53 in the inner side of the return springs 39 allows the return springs 39 to clear a pair of uprights 55 on the pivot bracket 36.

Figure 2C:
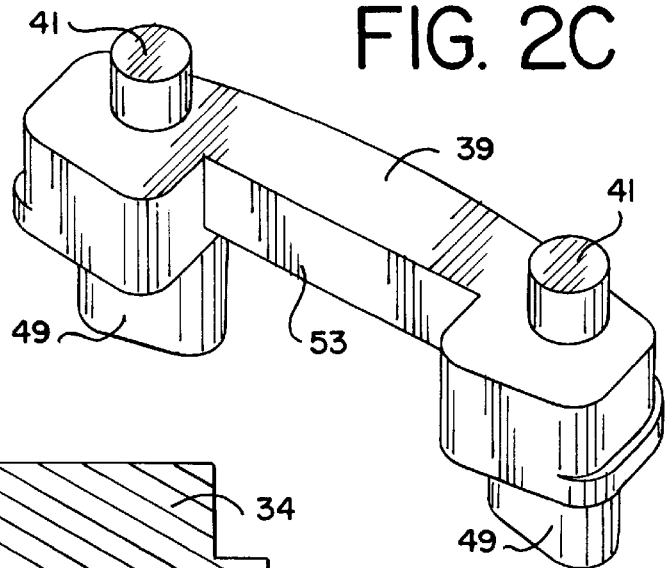
FIG. 2C is an isometric view the return spring shown in FIG. 2B.

FIG. 2C is an isometric view of the return spring 39 shown in FIG. 2B. As described above, the return spring 39 has two cylindrical projections 41, two feet 49 and a C-shaped recess 53.

Figure 2D:
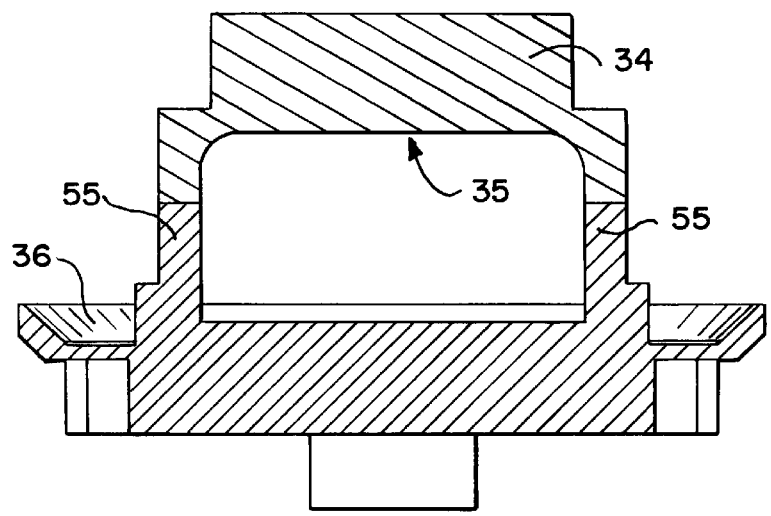
FIG. 2D is a sectional view of a pivot bracket shown in FIGS. 2A and 2B taken along the longitudinal axis of a pivot pin.
Figure 2E:
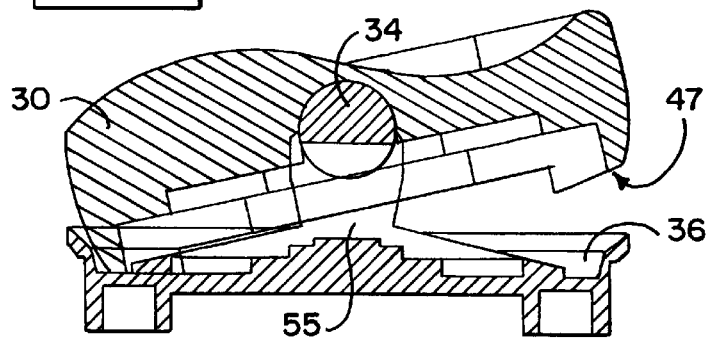
FIGS. 2E and 2F are sectional views of the control button, pivot bracket and pivot pin of the control device in which the control button is displaced to its full reverse and full forward positions, respectively.
Figure 2F:
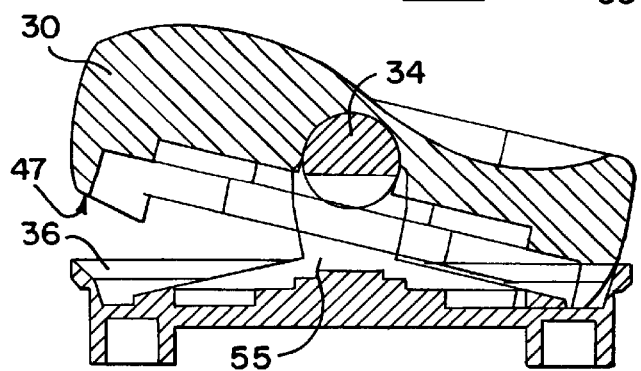

FIG. 2D is a sectional view of the pivot bracket 36, as shown in FIGS. 2A and 2B, taken along the longitudinal axis of the pivot pin 34. The pivot pin 34 is preferably formed from a ferromagnetic material, such as a martensitic (400 series) stainless steel. The pivot pin 34 may alternatively be formed from another corrosion-resistant ferromagnetic material, such as nickel. The pivot bracket 36, including the uprights 55, is preferably formed from a non-ferromagnetic material, such as brass.

The pivot pin 34 is preferably attached to the pivot bracket 36, such as by soldering the ends of the pivot pin 34 to the uprights 55. By attaching the pivot pin 34 to the pivot bracket 36, the reliability of the control device 28 may be improved and precise assembly may be simplified.

The control device 28 may be assembled by inserting the magnets, 38 and 40, and the shim 37 into the pivot bracket 36/pivot pin 34 structure shown in FIG. 2D. The shim 37 should extend evenly from both sides of the pivot pin 34 and should contact the flat surface 35 of the pivot pin 34. The two springs 39 are attached to the control button 30, such as by applying silicone rubber (RTV) to the cylindrical projections 41, inserting the cylindrical projections 41 into mating recesses in the control button 30, and curing the silicone rubber. The control button 30, including the return springs 39, is then attached to the shim 37 and magnets, 38 and 40, by applying, for example, an epoxy to the upper surfaces of the shim 37 and the magnets, 38 and 40. The epoxy should not contact the pivot pin 34. Once the control button 30 is attached to the shim 37 and magnets, 38 and 40, it may pivot in the pivot bracket 36 by sliding over the pivot pin 34. A commercially available epoxy that is suitable for this application is available from 3M Corp., Industrial Tape & Specialties Division, of St. Paul, Minn. as part no. DP-190 (gray).

In operation, the control button 30, shim 37 and magnets, 38 and 40, pivot about the corners of the flat surface 35 of the pivot pin 34 when the control button 30 is displaced by the user, as shown in FIGS. 2E and 2F. The return springs 39 preferably do not operate on the control button 30 when the control button 30 is positioned within approximately ±10% of its travel range from the neutral position. At such low tilt angles, the magnets 38 and 40 are sufficiently attracted to the flat surface 35 of the pivot pin 34 to cause a spontaneous return to the neutral position when the external force on the control button 30 is removed.

When the control button is displaced beyond approximately ±10% of its travel range, the return springs 39 press against the uprights 55 on the pivot bracket 36. Accordingly, the return springs 39 will act to return the control button 30 toward the neutral position when the external force on the control button 30 is removed.

When the control button 30 is displaced beyond approximately ±40% of its travel range, a foot 49 on each return spring 39 contacts the bottom of the pivot bracket 36. Again, the return springs 39 will act to return the control button toward the neutral position when the external force on the control button 30 is removed. The additional resistance provided by the feet may be required to overcome magnetic attraction between the hall shoe 46 and the nearest magnet, 38 or 40, which increases as the control button 30 is increasingly displaced from its neutral position.

In accordance with a preferred embodiment of the present invention, the ultrasound transducer 18 is stationary when the control button 30 is in the neutral position. On the other hand, when the control button 30 is tilted fully forward, as shown in FIGS. 1B and 2F, the ultrasound transducer rotates at its maximum speed in the forward direction. Likewise, when the control button 30 is fully tilted in the opposite direction, as shown in FIG. 2E, the ultrasound transducer preferably rotates at its maximum speed in the reverse direction. For purposes of this description, rotation in the forward direction refers to rotation toward the 180° position, while rotation in the reverse direction refers to rotation toward the 0° position.

A DC reference voltage is provided as an electrical input to the hall-effect sensor 42. When arranged as shown in FIG. 2A, the hall-effect sensor 42 generates an electrical output that is proportional in strength to the position of the control button 30 and, more particularly, to the position of the magnets 38 and 40.

For example, in a preferred embodiment the DC reference voltage is 8.0 volts and the hall-effect sensor 42 generates an electrical output of 4.0 volts when the control button 30 is in the neutral position. In addition, the hall-effect sensor generates an output of approximately 6.5 volts when the control button 30 is fully displaced in the forward direction and generates an output of approximately 1.5 volts when the control button 30 is fully displaced in the reverse direction. Because the control button 30 is continuously displaceable between its forward and reverse travel limits, the hall-effect sensor 42 produces an electrical output that falls within the range of approximately 1.5 volts to approximately 6.5 volts depending upon the position of the control button 30. The electrical output of the hall-effect sensor 42 preferably is linear over the 1.5–6.5 volt range. A hall-effect sensor 42 that is suitable for this application is commercially available from Honeywell Micro Switch of Freeport, Ill., Part No. SS89A1.

The control button 30, pivot bracket 36, magnets 38 and 40, and hall-effect sensor 42 form a bidirectional tilt switch or rocker switch. The switch generates an output electrical signal having a magnitude that corresponds to the position of the control button 30.

As shown in FIG. 2A, the upper surface of the control button 30 is preferably contoured or sculpted to improve the user's feel and to prevent the thumb or finger from slipping. Alternatively, the control button 30 may have a flat, concave or convex upper surface. It is also preferable that the side surfaces 43 of the control button 30 have a convex curvature, which allows the footprint of the control button 30 to remain nearly constant as the control button 30 rocks between the travel limits. As a result, the size of the opening in the control housing 12 surrounding the control device 28 may be minimized to prevent particulates from entering the opening and interfering with the operation of the control device 28 or causing premature wear.

Preferably, the footprint of the control button 30 is the same size as the footprint of the pivot bracket 36. In this case, the lower portion of the side surface 43 of the control button 30 should have a smaller radius of curvature than the upper portion of the side surface 43. For example, as shown in FIG. 2A, the upper portion of the side surface 43 has a 0.370" radius of curvature, while the lower portion has a 0.150" radius of curvature. The smaller radius of curvature on the lower portion of the side surface 43 ensures that there is no interference between the control button 30 and the pivot bracket 36. If space permits, the footprint of the pivot bracket 36 may, alternatively, be enlarged allowing the entire side surface 43 to be formed with the larger radius of curvature.

In addition, the control button 30 is formed from a non-ferromagnetic material. For example, when the control device 28 is mounted to the control housing 12 of the ultrasound probe 10, both the control housing 12 and the control button 30 may be polyurethane.

For the control device 28 as shown in FIG. 2A, the control housing 12 has a mating opening which receives the pivot bracket 36. The edges of the opening are secured by the fastener 32 between the clamp plate 45 and a flange 57 on the pivot bracket 36. A bead of silicone rubber, such as the RTV described above, is preferably applied between the flange 57 and the external surface of the control housing 12 to seal the control housing 12. Preferably, the fit between the pivot bracket 36 and the control housing 12 is tight enough to prevent significant stress on the seal when the control button 30 is operated. Toward this end, the pivot bracket 36 and the mating opening in the control housing 12 may be provided with keying features, such as tabs extending from the edges of the opening and mating recesses in the sides of the pivot bracket 36. Alternative methods for preventing relative motion between the pivot bracket 36 and the control housing 12 will be apparent to one skilled in the art.

Although the structure of the control device 28 as shown in FIG. 2A is preferred, the control device 28 may alternatively be implemented by securing the hall-effect sensor 42, the bracket 44 and the hall shoe 46 to an internal surface of the control housing 12. For this embodiment, the pivot bracket 36, which carries the control button 30 and the magnets 38 and 40, is secured to the external surface of the control housing 12 opposite the hall-effect sensor 42. Optionally, the pivot bracket 36 may be secured within a recess in the control housing 12. The wall of the control housing between the hall-effect sensor 42 and the pivot bracket 36 provides a hermetic seal in the area of the control device 28. The seal in the area of the control device 28 allows the probe 10 to be disinfected and/or sterilized without damaging structures within the control housing 12.

Referring now to FIG. 3, a schematic for processing a signal generated by the control device 28, shown in FIG. 2, to control rotation of the ultrasound transducer 18 is shown. The control device 28 is coupled to an amplifier/limiter 51. The output of the amplifier/limiter 51 is coupled to a low-pass filter 52. The output of the low-pass filter 52 is coupled to a deadband detector 54, a direction sensor 56 and a gain block 60. The output of the gain block 60 is coupled to a motor controller 62. The motor controller 62 is coupled to a motor 64, which rotates the ultrasound transducer 18.

The motor 64 is preferably located within the control housing 12 and coupled to the ultrasound transducer 18 by a flexible drive shaft located within the gastroscope tube 14. In addition, the motor is preferably a DC motor.

Figure 4:
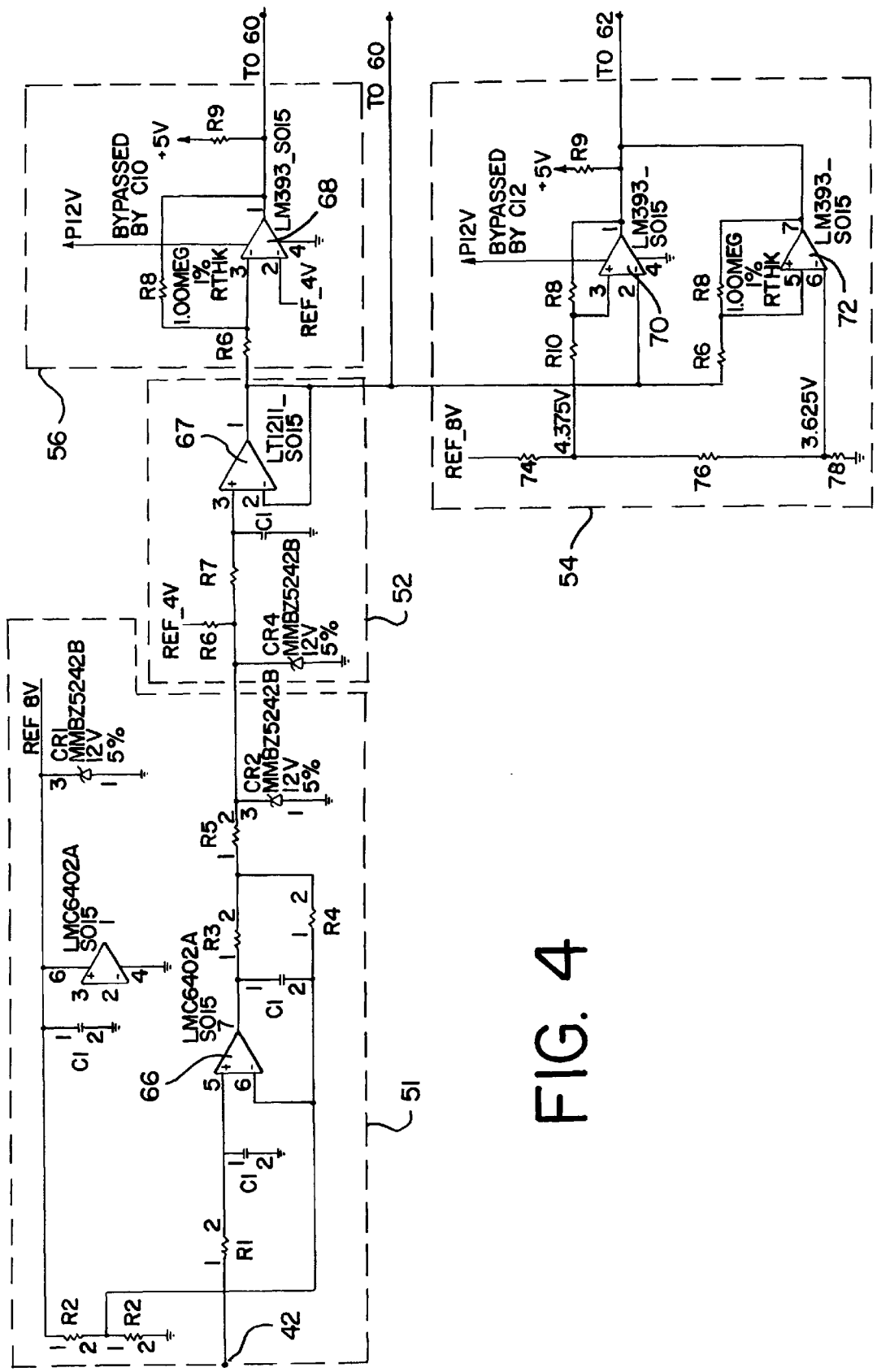
FIG. 4 is an electrical schematic showing preferred embodiments of an amplifier/limiter, a low-pass filter, a direction sensor and a dead band detector from the schematic of FIG. 3.

FIG. 4 is an electrical schematic showing preferred embodiments of the amplifier/limiter 51, the low-pass filter 52, the direction sensor 56 and the deadband detector 54 from the schematic of FIG. 3. Element valves for the electrical components shown in FIG. 4 are provided below in Table 1.

As shown in FIG. 4, the output of the hall-effect sensor 42 is provided to the amplifier/limiter 51. In particular, the hall-effect sensor 42 is coupled to the noninverting input of an operational amplifier 66. The operational amplifier 66 amplifies and clips the upper limits of the hall-effect signal to produce an output signal having the following characteristics: the output signal level is 6.6 volts, which corresponds to full speed forward, when the control button 30 of the control device 28 is displaced to its forward travel limit; the output signal level is 4.0 volts, which corresponds to zero speed, when the control button 30 of the control device 28 is in the neutral position; and the output signal level is 1.4 volts, which corresponds to full speed reverse, when the control button 30 of the control device 28 is displaced to its reverse travel limit.

The amplifier/limiter 51 is preferably located on a printed circuit board within the control housing 12. The operational amplifier 66 may be Part No. LMC6482AIM from National Semiconductor in Santa Clara, Calif.

The output of the operational amplifier 66 is coupled to the low-pass filter 52. In the low-pass filter 52, the output of the operational amplifier 66 is coupled to an operational amplifier 67. The low-pass filter 52 removes high frequency interference from the output of the amplifier/limiter 51, such as interference that may be caused by electronic surgical knives or other electronic devices operated within the vicinity of the ultrasound probe 10. For values of the resistor R7 and the capacitor C1 as given in Table 1, the low-pass filter 52 has a cut-off frequency of 16 Hz. The operational amplifier 67 is preferably Part No. LT1211CS8 from Linear Technology of Milpitas, Calif.

As shown in FIG. 4, the direction sensor 56 may be implemented by providing the output of the operational amplifier 67 to the noninverting input of a comparator 68. A 4 volt reference is coupled to the inverting input of the comparator 68. Accordingly, the output of the comparator 68 is a logic high-level signal when the control button 30 is unbalanced in the forward direction, i.e., the signal level of the output of the amplifier 66 is greater than 4 volts. On the other hand, the output of the comparator 68 is a logic low level signal when the control button 30 is unbalanced in the reverse direction, i.e., the signal level of the output of the amplifier 66 is less than 4 volts. As used herein, "forward" direction refers to that displacement of the control button 30 which causes rotation of the ultrasound transducer 18 toward its 180 degree position, and "reverse" direction refers to that displacement of the control button 30 which causes rotation of the ultrasound transducer 18 toward its zero degree position.

The deadband detector 54, shown in FIGS. 3 and 4, ensures that the motor 64 is off when the control button 30 is in its neutral position or only slightly out of balance. Preferably, the deadband detector 54 causes the motor 64 to remain off when the control button 30 is within approximately ±14% of its neutral position. When percentages are used herein to describe the position of the control button 30, the following convention is used: 0% is the neutral position, +100% is the maximum displacement in the forward direction, and −100% is the maximum displacement in the reverse direction. The inventor has found that a deadband improves the sonographer's "feel" for manual velocity control. In addition, the ±14% range provides some tolerance for the ability of the return springs 39 and the magnets 38 and 40 to return the control button 30 to its neutral position.

To implement the deadband detector 54, the hall-effect signal is coupled to two voltage comparators 70 and 72 in parallel. The upper and lower thresholds of the comparators 70 and 72 are set by resistors 74, 76 and 78 to produce the approximately ±14% deadband. For resistors 74, 76 and 78 having the values shown in Table 1, the output of the parallel comparators 70 and 72 is a logic low-level signal when the hall-effect signal is either greater than 4.375 volts or less than 3.625 volts. The output of the comparators 70 and 72 is a logic high-level signal when the hall-effect signal is between 3.625 volts and 4.375 volts.

TABLE 1

| R1 = 4.22 kΩ | R8 = 1.00 MΩ |
| R2 = 21.5 kΩ | R9 = 1.00 kΩ |
| R3 = 100 Ω | R10 = 6.81 kΩ |
| R4 = 6.19 kΩ | resistor 74 = 4.99 kΩ |
| R5 = 4.64 kΩ | resistor 76 = 1.10 kΩ |
| R6 = 10 kΩ | resistor 78 = 4.99 kΩ |
| R7 = 100 kΩ | C1 = 0.1 µF |

Referring again to FIG. 3, the motor controller 62 maintains the motor 64 in an off state until the signal from the deadband detector 54 goes low. If the output signal of the deadband detector 54 is a logic low-level signal, then the motor controller 62 obtains the desired motor velocity signal from the low-pass filter 52 via the gain block 60. As described above, the output of the deadband detector 54 goes low when the displacement of the control button 30, in either the forward or reverse direction, exceeds approximately 14%.

Figure 5:
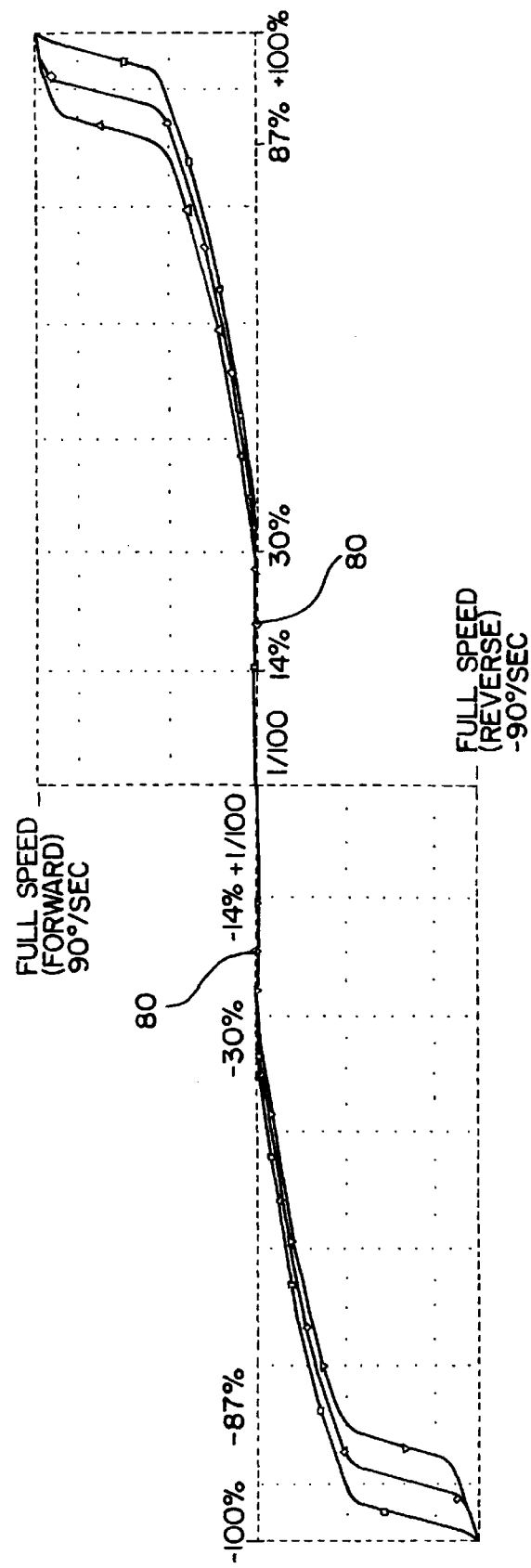
FIG. 5 is a graph of a preferred transfer characteristic for the gain block shown in FIG. 3.

FIG. 5 is a graph of a preferred transfer characteristic 61 for the gain block 60 shown in FIG. 3. The hall-effect sensor 42 produces, at the output of the low-pass filter 52, a signal that is linearly related to the position of the control button 30. With the understanding that the motor is to remain in the off state until the control button 30 is displaced, either in the forward or reverse direction, by more than approximately 14%, the remaining 14% to 100% displacement of the control button 30, in each direction, is mapped by the gain block 60 into a corresponding continuous range of rotational speeds.

Preferably, the continuous range of rotational speeds is broad, such as a range spanning 1/100th full speed to full speed, as shown in FIG. 5. For example, the embodiment described herein has a full speed of 90° per second. Accordingly, 1/100th full speed corresponds to 0.9° per second. Movement at low speeds, such as 0.9° per second, allows the sonographer to precisely position the ultrasound transducer 18 under manual control. At this speed, the sonographer may rotate the ultrasound transducer 18 one degree at a time. Movement at high speeds, on the other hand, allows the sonographer to quickly rotate the ultrasound transducer 18 in large increments, such as when switching between longitudinal and transverse views.

The mapping of control button 30 displacement into the continuous range of rotational speeds is preferably nonlinear. That is, for control button 30 positions within the approximately 14% to 100% range in each direction, the rate of change of rotational speed with respect to displacement of the control button 30 is not constant. In the preferred embodiment, the transfer characteristic 61 of the gain block 60 favors the slower speeds. The majority of the 14% to 100% range is dedicated to slow and moderate speeds, as shown in FIG. 5, for precise manual position control. This means that, in general, the rate of change of rotational speed is lower when the control button 30 is nearer to its balanced or neutral position than when the control button 30 approaches the limits of its range of displacement.

In FIG. 5, the transfer characteristic 61 of a preferred nonlinear gain block 60 is plotted with the gain block output on the vertical axis and the gain block input on the horizontal axis. The gain block 60 transforms an input representing the position of the control button 30 into an output representing the desired velocity. The gain block output, which is coupled to the motor controller 62, corresponds to the desired velocity of the ultrasound transducer 18. The gain block input, which is provided by the low-pass filter 52, corresponds to the percentage of displacement of the control button 30. Preferably, the transfer characteristic 61 of the gain block 60 is continuous as the motor speed increases from 1/100th speed to full speed, as shown in FIG. 5. As used herein, a "continuous" transfer characteristic is one having finite slope over a range of motor speeds.

As shown in FIG. 5, the transfer characteristic 61 includes two flat areas 80, which correspond to displacement of the control button 30 within the range of approximately the neutral position (0%) to approximately 30%, and the neutral position (0%) to approximately −30%. When the control button 30 is positioned within the positive portion of this range, the gain block output is fixed at 1/100th full speed in the forward direction. Similarly, when the control button 30 is positioned within the 0 to −30% portion of this range, the gain block is fixed at 1/100th full speed in the reverse direction. The flat areas 80 are desirable because they allow the sonographer to displace the control button 30 to a range of positions beyond the ±14% deadband zone, while remaining at the slowest speed. Accordingly, the flat areas 80 provided by the gain block 60 provide the advantage of improving the sonographer's feel of control at slow speeds.

Between approximately 30% and 87% of full displacement of the control button 30 in each direction, the transfer characteristic 61 is approximately linear. When the control button 30 is displaced beyond approximately 87% in each direction, the output of the gain block quickly increases to full speed.

Figure 6A:
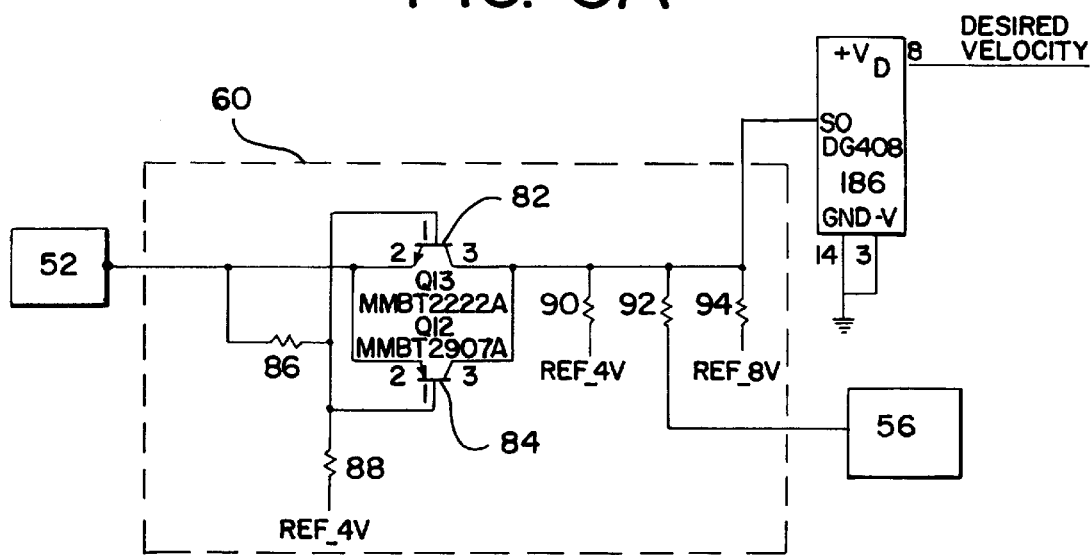
FIGS. 6A and 6B are electrical schematics for producing the transfer characteristic shown in FIG. 5.
Figure 6B:
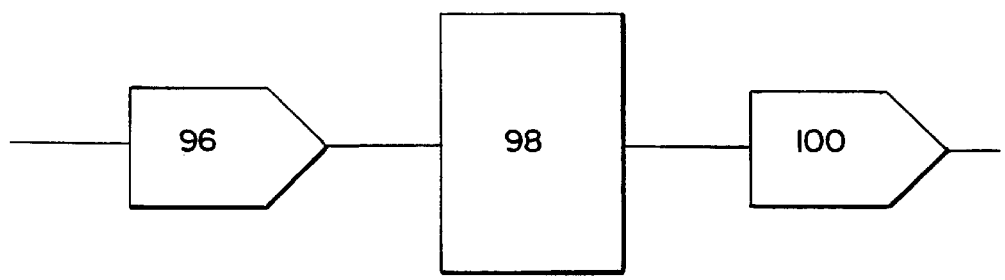

FIGS. 6A and 6B are electrical schematics for producing the transfer characteristic shown in FIG. 5. In FIG. 6A, the output of the low-pass filter 52 is coupled to the emitters of transistors 82 and 84. The output of the low-pass filter 52 is also coupled through resistor 86 to the base of transistors 82 and 84. A 4 volt DC reference voltage is applied to the base of transistors 82 and 84 through a resistor 88. The collectors of the transistors 82 and 84 are coupled. The resistor 90 couples the collectors to a 4 volt DC reference voltage. The resistor 92 couples the collectors to the output of the direction sensor 56, which is shown in FIGS. 3 and 4. Finally, a resistor 94 couples the collector to an 8 volt DC reference voltage.

The transistor 82 is an NPN bipolar junction transistor, such as Part No. MMBT2222A manufactured by Motorola of Phoenix, Ariz. The transistor 84 is a PNP bi-polar junction transistor, such as Part No. MMBT2907A, also manufactured by Motorola. Resistors 86, 88, 90, 92 and 94 have resistance values as shown in Table 2. The resistors are preferably implemented in thick film on a printed circuit board and have a 1% tolerance.

TABLE 2

| |
|---|
| Resistor 86 = 2.15 kΩ |
| Resistor 88 = 4.64 kΩ |
| Resistor 90 = 1.00 kΩ |
| Resistor 92 = 100 kΩ |
| Resistor 94 = 261 kΩ |

The operation of the gain block 60 shown in FIG. 6A will now be described. As the control button 30 is displaced from its neutral position toward the forward direction, the output of the low-pass filter 52, shown in FIG. 4, begins to increase from 4.0 volts DC. This output from the low-pass filter 52 becomes an input to the gain block 60 and is coupled to the emitters and bases of the transistors 82 and 84 as shown in FIG. 6A. When the input voltage is between approximately 4.0 volts and 4.7 volts, the transistors 82 and 84 are off and the voltage at the collectors of the transistors 82 and 84 stays fixed, as determined by the values of the resistors 90, 92 and 94. In the present embodiment, the chosen resistor values maintain the collector voltage at the level corresponding to 1/100th of the full speed, thereby creating the flat spot in the speed control curve.

The rotational speed that corresponds to the flat spot in the speed control curve may be adjusted by changing the resistance value of the resistor 92. For example, the fixed minimum speed will increase as the resistance of the resistor 92 is decreased.

Within the 30% to 80% range of control button 30 positions, the base-collector junction of either transistor 84 or transistor 82 turns on due to current flowing through the resistor 86. More specifically, when the control button 30 is located within the 30% to 87% range in the forward direction, the transistor 82 turns on, and when the control button 30 is located within the 30% to 87% range in the reverse direction, the transistor 84 turns on. For control button 30 positions within these ranges, the collector voltage varies almost linearly with the output of the low-pass filter 52.

At approximately the 87% point in the displacement of the control button 30, the transistor 82 or 84 becomes fully turned on. This causes a rapid increase to full speed with further control button 30 displacement. The point at which the transistors 82 and 84 become fully turned on is determined by the resistors 86 and 88. For example, by decreasing the resistance value of the resistor 86 with respect to the value of the resistor 88, the point at which the gain block output begins to quickly increase can be moved to the left in FIG. 5. Accordingly, the shape of the nonlinear transformation performed by the circuit of FIG. 6A can be changed by varying the values of the resistors.

The 1/100th speed and the full speed as determined by the transfer characteristic 61 of the gain block 60 preferably are independent of temperature under normal operating conditions. As shown in FIG. 5, 1/100th speed and full speed for the gain block circuit of FIG. 6A are constant for temperatures of 0° C., 25° C. and 50° C.

An alternative embodiment of the gain block 60 is shown in FIG. 6B. The output of the low-pass filter 52 is provided to an analog-to-digital converter 96. The analog-to-digital converter 96 converts the analog output of the low-pass filter 52 into a digital signal. The digital signal from the analog-to-digital converter 96 is coupled to a memory module 98. The memory module 98 provides a predetermined output corresponding to the digital input. The predetermined output is coupled from the memory module 98 to a digital to analog converter 100, which is then coupled to the motor controller 62 shown in FIG. 3.

In the alternative embodiment, the memory module 98 may be an Erasable Programmable Read Only Memory ("EPROM") having 8 bit address and data lines, in which case the converters 96 and 100 will also be 8 bit converters. The memory module 98 is programmed to give a conversion, or look-up table, between the input digital value and the desired output digital value. For an 8 bit memory module, the input voltage range may be quantized into 256 discrete levels by the 8 bit analog-to-digital converter 96. The digital output of the analog-to-digital converter 96 drives the address lines of the EPROM. For each address input, there is a corresponding data output. For this embodiment, the amplifier/limiter 51 preferably produces an output between 0 volts and 5 volts, with 0 volts corresponding to the reverse travel limit of the control button 30 and 5.0 volts corresponding to the forward travel limit of the control button 30. By using a digital nonlinear gain block as shown in FIG. 6B, the shape of the nonlinear gain block can be tailored in accordance with the intended application by storing appropriate data in the EPROM.

Figure 7A:
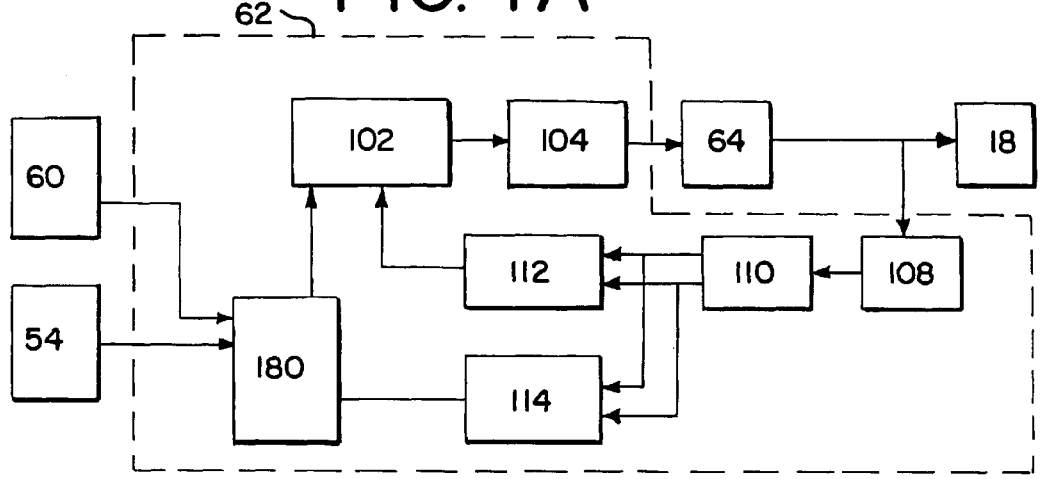
FIG. 7A is a block diagram of a preferred embodiment of the motor controller shown in FIG. 3.

FIG. 7A is a block diagram of a preferred embodiment of the motor controller 62 shown in FIG. 3. The output of the gain block 60 is coupled to a velocity servo 102. An output of the velocity servo 102 is coupled to a motor driver 104 which is in turn coupled to the motor 64. The motor 64, which is preferably a DC motor, has a shaft that is mechanically coupled to the ultrasound transducer 18.

An encoder 108 is coupled to the motor 64. The encoder 108 is preferably a quadrature encoder that is mounted to the shaft of the motor 64. The encoder 108 may be a standard two-channel quadrature encoder that produces a logic level transition at the rate of 16 transitions per motor shaft revolution. A DC motor and a quadrature encoder that are suitable for this application are available from MicroMo of St. Petersburg, Fla., Part Nos. 1331T-012S and HEM-1516-16, respectively.

As shown in FIG. 7A, an output from the encoder 108 may be provided to a detector 110. The detector 110 is coupled to a velocity detector 112, which is in turn coupled to the velocity servo 102.

The detector 110 may produce two output signals. A first output signal 111 represents the direction in which the motor shaft is turning, and a second output signal 113 being a train of pulses whose frequency represents the motor velocity. The velocity detector 112 converts the two signals 111 and 113 into a voltage that is proportional to the actual motor velocity and provides that voltage to the velocity servo 102.

During rotation of the ultrasound transducer 18, the velocity servo 102 compares the desired velocity, as represented by the output of the gain block 60, with the actual velocity, as represented by the output of the velocity detector 112. The velocity servo 102 amplifies any difference between the actual velocity and the desired velocity. This signal becomes the input to the motor driver 104. The motor driver 104 preferably operates in a linear voltage mode, i.e., a linear change in the output of the velocity servo 102 produces a linear change in the voltage applied to the motor 64.

The detector 110 may also be coupled to an up/down counter 114, as shown in FIG. 7A. The up/down counter 114 provides three signals to a motor disable circuit 180. The motor disable circuit 180 also receives the outputs of the deadband detector 54 and the gain block 60. The operation of the motor disable circuit is described below in reference to FIG. 10.

In a preferred mode of operation, the system is initialized by resetting the up/down counter 114 and rotating the ultrasound transducer 18 to its 0 degree position upon start up. In this manner, the up/down counter 114 keeps track of the position of the ultrasound transducer 18 with respect to its 0 degree position by monitoring the output of the detector 110. Preferably, a microprocessor 184, shown in FIG. 8, initializes the system.

Figure 7B:
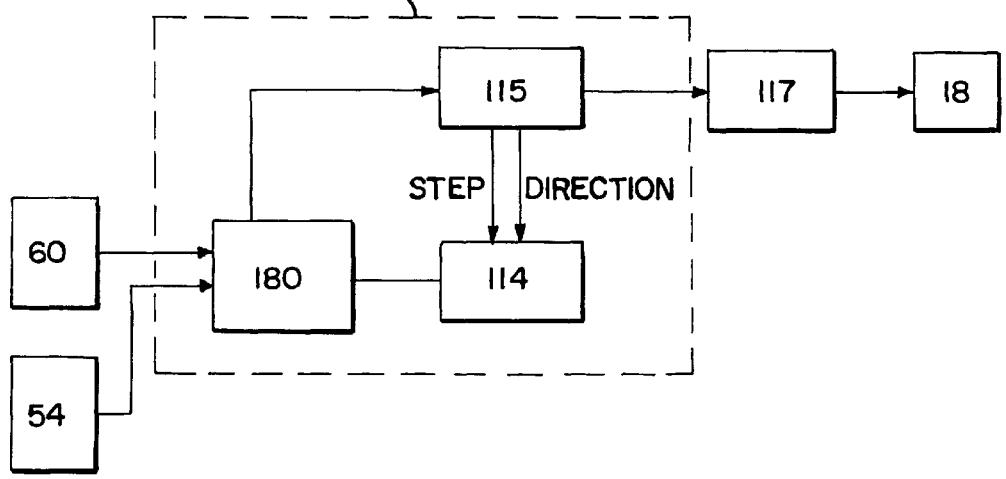
FIGS. 7B and 7C are block diagrams of alternative embodiments of the motor controller shown in FIG. 3.
Figure 7C:
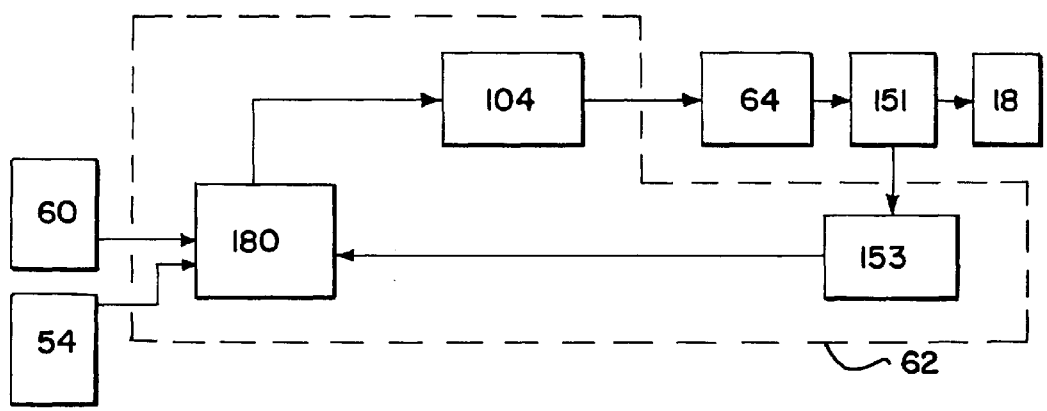

FIGS. 7B and 7C are block diagrams of alternative embodiments of the motor controller 62 shown in FIG. 3. In FIG. 7B, the motor controller 62 is a stepper motor driver 115 coupled to the up/down counter 114. The stepper motor driver 115 is also coupled to a stepper motor 117.

The stepper motor driver 115 provides both a step signal and a direction signal to the up/down counter 114, as shown in FIG. 7B. The up/down counter 114 generates a signal representing the position of the ultrasound transducer 18 from the step signal and the direction signal. The output of the up/down counter 114 is coupled to the motor disable circuit 180. The motor disable circuit 180 also receives inputs from the gain block 60 and the deadband detector 54. An output of the motor disable circuit 180 is coupled to the stepper motor driver 115. A disadvantage of the embodiment shown in FIG. 7B is that switching stepper motor noise may interfere with the ultrasound image.

FIG. 7C shows an alternative arrangement for controlling the position of the ultrasound transducer 18. A motor driver 104 is coupled to a DC motor 64. A gear box 151 couples the DC motor 64 to a ten-turn potentiometer 153. The gear box 151 provides gear reduction between the DC motor 64 and the potentiometer 153. The potentiometer 153 is coupled to the motor disable circuit 180, which also receives inputs from the gain block 60 and the deadband detector 54. The motor disable circuit 180 is coupled to the motor driver 104. A disadvantage of the embodiment of FIG. 7C is that the gear box 151 introduces backlash, which may create error in the potentiometer's ability to measure the position of the motor shaft. In addition, the potentiometer 153 is prone to early mechanical failure as compared to the encoder approach. The embodiment shown in FIG. 7A is, therefore, preferred.

Figure 8:
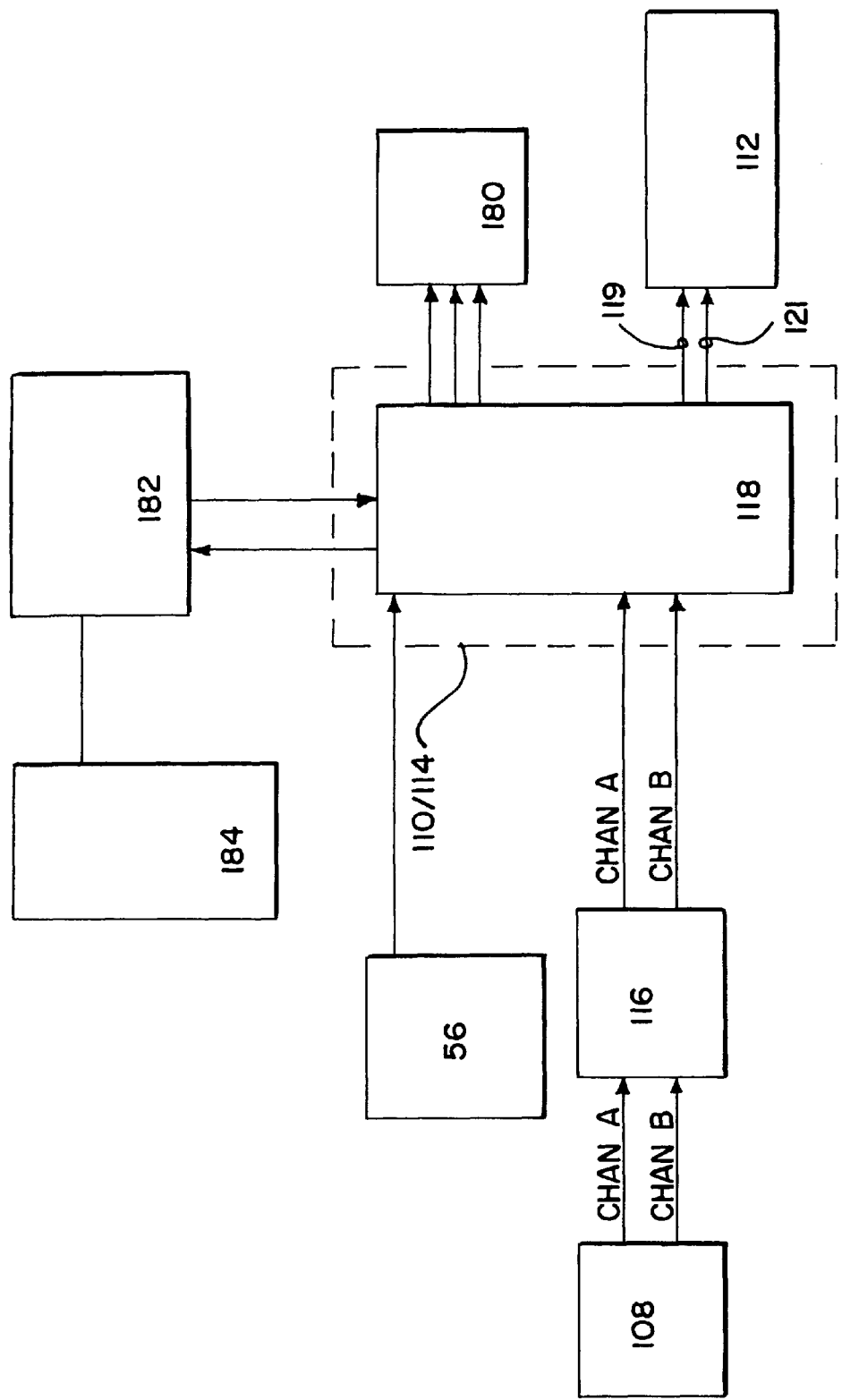
FIG. 8 is an electrical schematic of preferred embodiments of the detector and up/down counter shown in FIG. 7A.

FIG. 8 is an electrical schematic of preferred embodiments of the detector 110 and up/down counter 114 shown in FIG. 7A. As described above, the encoder 108 produces two logic level signals, which are shown in FIG. 8 as Channel A and Channel B. For each channel, the encoder 108 produces 16 encoder transitions per motor shaft revolution. As shown in FIG. 8, the signals Channel A and Channel B are coupled by logic buffers 116 to a field programmable gate array ("FPGA") 118. The FPGA 118 performs the functions of the detector 110 and up/down counter 114 shown in FIG. 7A. A commercially available FPGA that is suitable for this application is made and sold by XILINX, Inc. of San Jose, Calif., as Part No. XC4005A-5TQ144C.

The FPGA 118 generates a logic level signal 119 that indicates the direction in which the motor is moving and also generates a pulse train 121 having 64 pulses per motor shaft revolution. The FPGA 118 uses these two signals to control an internal up/down counter thereby keeping track of the motor position. The two signals generated by the FPGA 118 are also used externally to determine the motor velocity by coupling them to the velocity detector 112.

As shown in FIG. 8, the FPGA 118 preferably is in serial communication with a microprocessor 184 through a memory module 182. The memory module 182 is preferably a dual port 2k by 8 bit random access memory. In the preferred mode of operation, the microprocessor 184 initializes the FPGA 118 by instructing the FPGA 118 to rotate the ultrasound transducer 18 to its home position and resetting the internal counter of the FPGA 118.

The FPGA 118 provides the advantage of monitoring the position of the ultrasound transducer 18 without the application of a system clock, which may generate electrical noise that interferes with imaging. The FPGA 118 is configured as a state-machine, keeping track of the ultrasound transducer 18 position, the motor 64 speed and end-of-travel limits without the need for a continuous clock. The system clock may then be applied to the FPGA 118 for a very short burst between ultrasound image frames for quick serial communication between the FPGA 118 and the microprocessor 184.

Figure 9E:
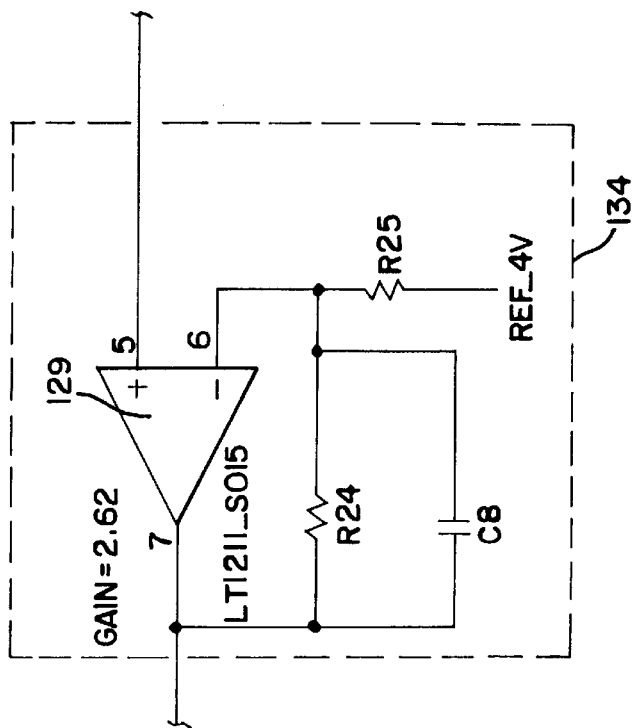

FIGS. 9A and FIGS. 9B through 9F are a block diagram and an electrical schematic, respectively, of the velocity detector 112 and velocity servo 102 shown in FIG. 7A. As shown in FIG. 9A, the velocity detector 112 includes a one-shot converter circuit 120 that is coupled to the pulse train output 121 of the FPGA 118. The one-shot converter circuit 120 converts the variable width pulses of the FPGA output signal 121 into a signal having pulses with precisely controlled pulse width.

The output 123 of the one-shot converter circuit 120 and the encoder direction signal 119 generated by the FPGA 118 are provided as inputs to a velocity polarity restorer circuit 122, as shown in FIGS. 9A and 9C. The velocity polarity restorer circuit 122 operates to precisely control the amplitude of the pulse train, and produces a DC output corresponding to the average voltage of the pulse train.

Referring again to FIG. 9A, the output of the velocity polarity restorer circuit 122 is coupled to a velocity ripple filter 132, which removes ripple from the DC output of the velocity polarity restorer circuit 122. The velocity ripple filter 132 is coupled to a velocity sensor full-scale adjust circuit 134, which amplifies the output of the filter 132. The output of the velocity sensor full-scale adjust circuit 134 is coupled to the velocity servo 102.

FIG. 9B is an electrical schematic of the one-shot converter circuit 120. The pulse train output 121 of the FPGA 118 is coupled to the trigger of one-shot converter 210. A one-shot converter 210 that is suitable for this application is available from National Semiconductor, Part No. LM555CM. The resistors, R20 and R21, and the capacitors, C1 and C2, have values as shown in Table 3. As shown in FIG. 9B, the one-shot converter circuit 120 produces, for each input pulse, an output pulse with a 51 microsecond pulse width.

FIG. 9C is an electrical schematic of the velocity polarity restorer circuit 122. As shown in FIG. 9C, the output signal 123 from the one-shot converter circuit 120 and the encoder direction signal 119 from the FPGA 118 are supplied as inputs to a multiplexer 124 in the velocity polarity restorer circuit 122. The output of the multiplexer 124 is a pulse train 125 in which the pulses have precise amplitude and width.

In the absence of a one-shot pulse, a switch S2-D2 of the multiplexer 124 in the velocity polarity restorer circuit 122 is opened. In this condition, the noninverting input to an operational amplifier 126 is held at 4.0 volts by a resistor 128 and a 4 volt reference voltage. When a pulse arrives, the switch S2-D2 of the multiplexer 124 is closed for the duration of the pulse causing the resistor 128 to be pulled toward 0 volts or 8 volts through the resistor 130, depending upon the state of the encoder direction signal 119. Component values for the resistors 128 and 130 and the capacitor C3 are provided in Table 3 below.

The average voltage of the precision amplitude precision width pulses at the output of the multiplexer 124 is proportional to the actual motor velocity. The velocity polarity restorer circuit 122 restores the sign of the velocity with reference to the 4 volt reference voltage in order to tell the difference between forward velocities and reverse velocities.

The DC output of the velocity polarity restorer circuit 122 is coupled to the velocity ripple filter 132. An electrical schematic of the velocity ripple filter is shown in FIG. 9D. At very slow speeds, encoder pulses in the train are coming infrequently, which causes unwanted ripple in the average DC voltage at the output of the velocity polarity restorer circuit 122. Accordingly, the velocity ripple filter 132, as shown in FIGS. 9A and 9B, removes the encoder ripple from the average DC level without substantially increasing time delay.

As shown in FIG. 9D, the velocity ripple filter 132 is preferably a three-pole Chebychev low-pass filter with 0.5 dB passband ripple and a cut-off frequency at 410 Hz. The output of the velocity polarity restorer circuit 122 is coupled through three resistors R22 to the noninverting input of an operational amplifier 127. The output of the operational amplifier 127 is coupled to the velocity sensor full-scale adjust circuit 134. Although a three-pole Bessel filter may alternatively be used to achieve less overshoot, the three-pole Chebychev filter provides a slight improvement in rise time and more stability in the feedback loop.

The velocity sensor full-scale adjust circuit 134 amplifies the output of the velocity ripple filter 132 so that a full-speed signal produces 6.5 volts if the motor is turning in the forward direction or 1.5 volts if the motor is turning in the reverse direction.

As shown in FIG. 9E, the output of the velocity ripple filter 132 is coupled to the noninverting input of an operational amplifier 129. The inverting input of the operational amplifier 129 is coupled through a resistor R25 to a 4 volt reference. A resistor R24 and a capacitor C8 are coupled between the output of the operational amplifier 129 and its inverting input. The output signal 136 of the velocity sensor full-scale adjust circuit 134 is a DC voltage level corresponding to the actual velocity of the motor 64. Component values for the resistors R24 and R25 and the capacitor C8 are provided below in Table 3.

Figure 9F:
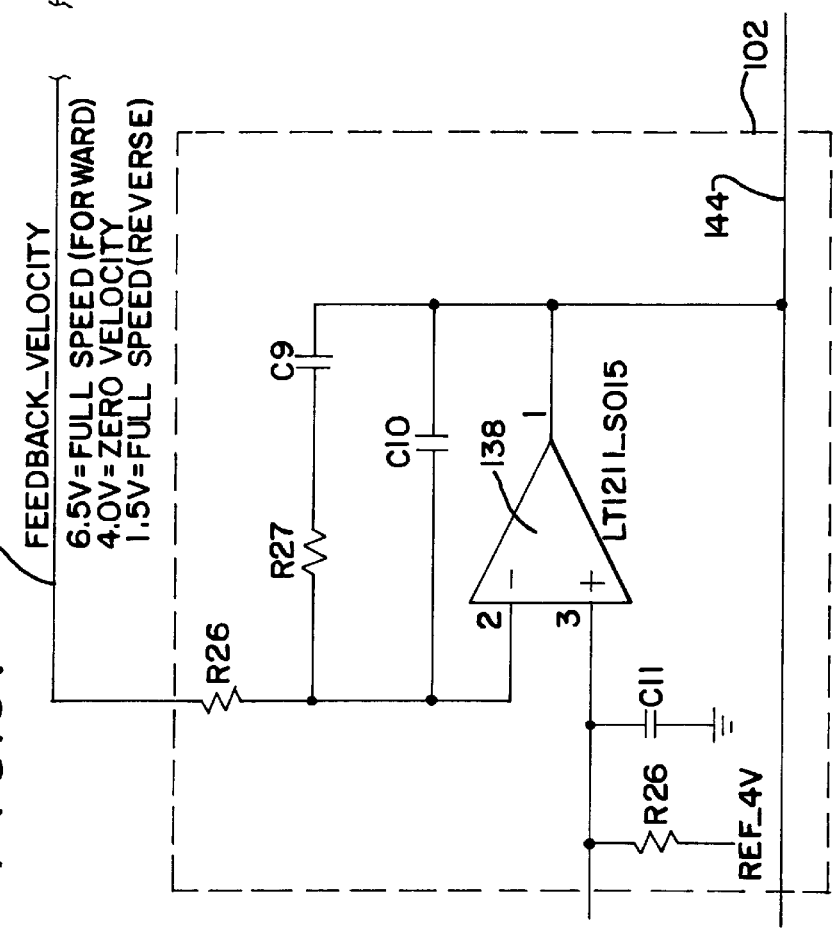

FIG. 9F is an electrical schematic of the velocity servo 102. The output of the operational amplifier 129 is coupled through a resistor R26 to an operational amplifier 138. A capacitor C10 is coupled between the output of the operational amplifier 138 and its inverting input. The output of the operational amplifier 138 is also coupled through a resistor R27 and a capacitor C9 to the resistor R26. A 4 volt reference is coupled to the noninverting input of the operational amplifier 138 through a resistor R26. A capacitor C11 is coupled between the noninverting input and ground.

Component values for the resistors R26 and R27 and the capacitors C9, C10 and C11 are provided below in Table 3. The operational amplifiers 126, 127, 129 and 138 are preferably Part No. LT1211CS8 from Linear Technology of Milpitas, Calif.

TABLE 3

| | |
|---|---|
| R20 = 46.4 kΩ, .1%, THN | C1 = 0.1 μF |
| R21 = 4.64 kΩ, .1%, THK | C2 = 1.0 nF COG 1% 50 v |
| R22 = 42.2 kΩ, .1%, THN | C3 = 1.0 nF COG 1% 50 v |
| R23 = 121 kΩ, .1%, THN | C4 = 22 nF X7R 10% 50 v |
| R24 = 16.2 kΩ, .1%, THN | C5 = 100 nF X7R 10% 50 v |
| R25 = 10 kΩ, .1%, THN | C6 = 820 pF COG 5% 100 v |
| R26 = 10 kΩ, .1%, THN | C7 = 100 pF COG 5% 100 v |
| R27 = 31.6 kΩ, .1%, THN | C8 = 100 pF COG 1% 100 v |
| | C9 = 820 nF X7R 10% 50 v |
| Resistor 128 = 10.0 kΩ, .1%, THN | C10 = 22 nF X7R 10% 50 v |
| Resistor 130 = 6.19 kΩ, .1%, THN | C11 = 1.0 nF COG 1% 50 v |

The velocity servo 102 compares the actual velocity of the motor 64, as represented by the output of 136 of the full-scale adjust circuit 134, with a desired motor velocity, as represented by a signal 188 provided by the motor disable circuit 180. The operational amplifier 138 generates a output signal 144 representing the integrated difference between the actual velocity signal 136 and the desired velocity signal 188. The output signal 144 is coupled to the motor driver 104, shown in FIGS. 7A and 11, which directly controls the motor velocity.

Figure 10:
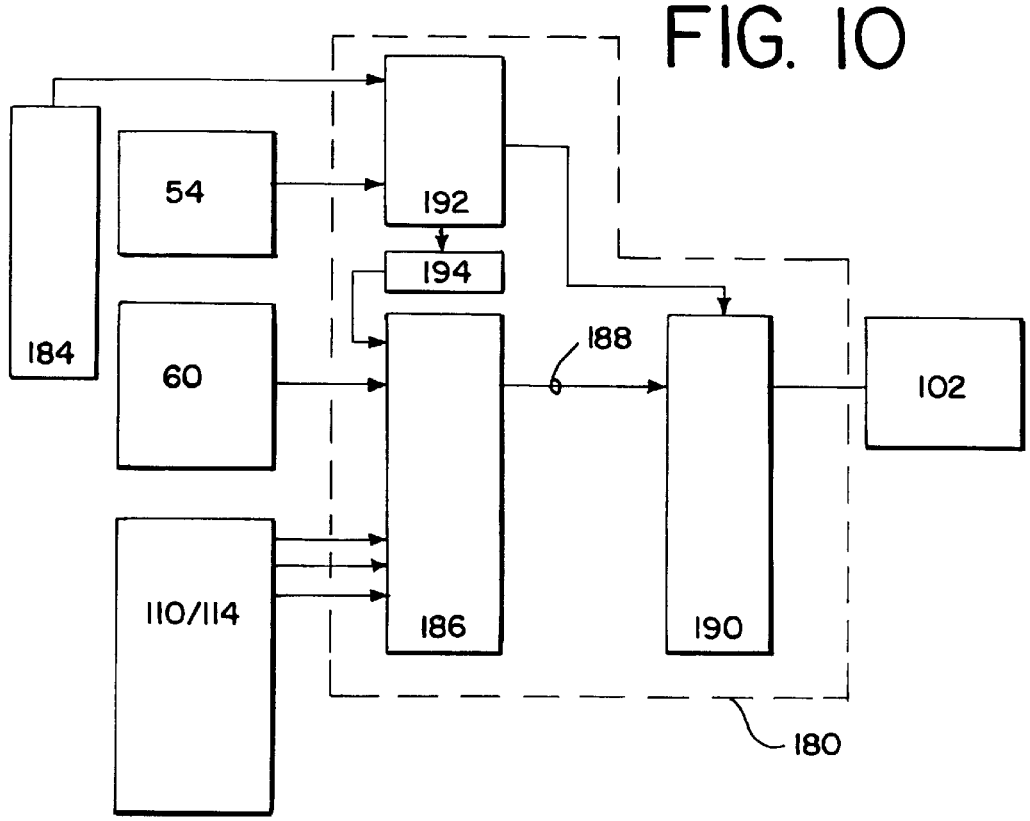
FIG. 10 is a schematic of the motor disable circuit shown in FIG. 7A.

FIG. 10 is an electrical schematic of the motor disable circuit 180 shown in FIG. 7A. The detector and up/down counter 110/114 and the gain block 60 are coupled to a multiplexer 186. A remote speed-setting circuit 194 is also coupled to the multiplexer 186. The deadband detector 54 and the microprocessor 184 are coupled to a second multiplexer 192. The multiplexer 192 is coupled to the remote speed-setting circuit 194 and a switch 190. The switch 190 is coupled to the velocity servo 102.

In operation, the multiplexer 186 selects the desired velocity from either the gain block 60 or the remote speed-setting circuit 194 in accordance with the three velocity bits, which form a speed selection signal, provided by the up/down counter 114 of the FPGA 118. When the probe 10 is used in the manual mode by moving the control button 30, as indicated by the speed selection signal, the multiplexer 186 selects the desired velocity signal from the gain block 60.

On the other hand, when the speed selection signal from the up/down counter 114 of the FPGA 118 indicates that the probe 10 is to operate in the remote mode, the multiplexer 186 selects one of several predetermined velocities from the remote speed-setting circuit 194 in accordance with the speed selection signal. When the probe 10 operates in a remote mode, the microprocessor 184 provides a direction selection signal to the second multiplexer 192. The multiplexer 192 responds to the direction selection signal by coupling an appropriate reference voltage, 8.0 volts for forward and 0 volts for reverse, to the speed-setting circuit 194. The desired velocity signal is then selected by the multiplexer 186 from the speed-setting circuit 194 and is provided to the switch 190 on the signal line 188.

In a preferred embodiment for remote operation, the desired velocity on the signal line 188 may be set to zero or one of six fixed speeds in either the forward or reverse direction. The multiplexer 186 is provided with eight selectable inputs: one for each of the six fixed speeds, zero and the manual input from the gain block 60. The multiplexer 186 then selects the desired input in accordance with the three velocity bits from the up/down counter 114 of the FPGA 118.

The six fixed speeds may be provided by the remote speed-setting circuit 194 to the multiplexer 186 as follows. The remote speed-setting circuit 194 is formed by connecting a first end of six resistors, R28, R29, R30, R31, R32 and R33, to a common node. The common node may be coupled through the multiplexer 192 to either the 8.0 volt reference or the 0 volt reference. The values of the resistors, and the corresponding speeds as a fraction of full speed, are provided below in Table 4. A second end of each resistor, R28 through R33, is coupled to a separate selectable input of the multiplexer 186.

While the speed of the motor is determined by the value of the resistor R28 through R33 in the speed-setting circuit when in the remote mode, the direction is determined by the microprocessor 184. When the microprocessor 184 provides a signal to the multiplexer 192 indicating that the ultrasound transducer 18 is to rotate in the forward direction, the multiplexer 192 couples the 8.0 volt reference to the common node. On the other hand, when the microprocessor 184 provides a signal to the multiplexer 192 indicating that the ultrasound transducer 18 is to rotate in the reverse direction, the multiplexer 192 couples the common node to ground.

TABLE 4

| |
|---|
| R28 = 147 kΩ, .1%, THN, 1/10 speed |
| R29 = 121 kΩ, .1%, THN, 1/8 speed |
| R30 = 56.2 kΩ, .1%, THN, 1/4 speed |
| R31 = 21.5 kΩ, .1%, THN, 1/2 speed |
| R32 = 11.0 kΩ, .1%, THN, 3/4 speed |
| R33 = 6.19 kΩ, .1%, THN, full speed |

The selected resistor from the remote speed-setting circuit 194 forms a voltage divider with the resistor R26, shown in FIG. 9F, that is coupled between the noninverting input of the operational amplifier 138 and the 4 volt reference. The speed corresponding to each resistor, R28 through R33, is provided above in Table 4. When no resistor is selected by the multiplexer 186, the 4 volt reference, which corresponds to zero velocity, is applied to the operational amplifier 138 as the desired velocity.

The second multiplexer 192 controls the state of the switch 190 in accordance with the inputs from the deadband detector 54 and the microprocessor 184. If, for example, the deadband detector 54 indicates that the control button 30 is positioned within the ±14% deadband zone, then the switch 190 remains open and the desired velocity on the signal line 188 is not provided to the velocity servo 102.

Preferably, the switch 190 couples the signal 188 to the operational amplifier 138 of the velocity servo 102 whenever the motor 64 is supposed to be moving. Conversely, the switch 190 preferably blocks the signal 188 when the control button 30 is in its neutral position, when the ultrasound transducer 18 reaches its end-of-travel limits, or when a stalled motor 64 is detected. As noted above, the state of the switch 190 is controlled by second multiplexer 192 of the motor disable circuit 180, as shown in FIG. 10.

During use of the probe 10, the operational amplifier 138 compares the desired velocity signal 188, which derives from the position of the control button 30, to an actual velocity signal 136, which derives from the encoder 108, to control rotation of the ultrasound transducer 18. In order to improve the performance of the motor controller, it is, therefore, desirable that the time delay in the path of the actual velocity signal 136 be minimized. The embodiments of the elements in the feedback path of the actual velocity signal, as shown in FIGS. 8 and 9, reflect this design consideration.

The accuracy of the motor speed control described herein depends primarily upon the tolerances of the resistors in Table 4, the tolerance of the resistor R26, the accuracy of the voltage references and the one-shot pulse width. The circuitry described herein provides accuracy to within approximately ±5%, independent of the friction on the motor 64.

Figure 11:
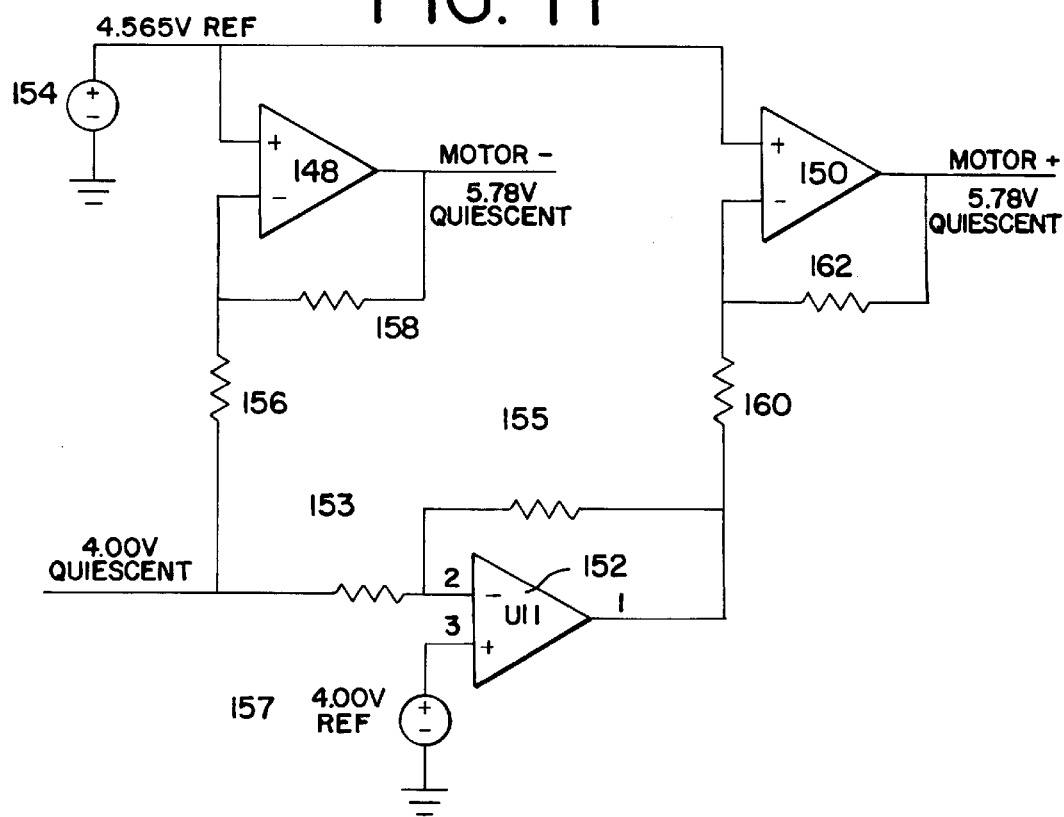
FIG. 11 is an electrical schematic of the motor driver shown in FIG. 7A.

FIG. 11 is an electrical schematic of the motor driver 104 shown in FIG. 7A. The motor driver 104 includes two power operational amplifiers 148 and 150 and an inverter 152. A 4.565 volt DC reference 154 is coupled to the noninverting inputs of the power operational amplifiers 148 and 150. The inverter 152 includes an input resistor 153 and a feedback resistor 155, which have the same resistance value of 10 kΩ, and therefore produce unity gain. The noninverting input of the inverter 152 is coupled to a 4.0 volt DC reference 157.

The signal 144 is coupled to the inverting input of the power operational amplifier 148 through a resistor 156. A feedback resistor 158 is connected between the output of the power operational amplifier 148 and its inverting input. The resistor 156 is 10 kΩ and the resistor 158 is 21.5 kΩ. The gain of the power operational amplifier 148, which is determined by the ratio of the resistances of the feedback resistor 158 with respect to the resistor 156, is 2.15. The output of the power operational amplifier 148 is coupled to the negative terminal of the motor 64.

As shown in FIG. 11, the signal 144 is also coupled to the inverting input of the power operational amplifier 150 through the inverter 152 and a resistor 160. A feedback resistor 162 is connected between the output of the power operational amplifier 150 and its inverting input. The resistor 160 is 10 kΩ and the resistor 162 is 21.5 kΩ. The gain of the power operational amplifier 150, which is determined by the ratio of the resistances of the feedback resistor 162 with respect to the resistor 160, is 2.15. The output of the power operational amplifier 150 is coupled to the positive terminal of the motor 64.

Figure 12:
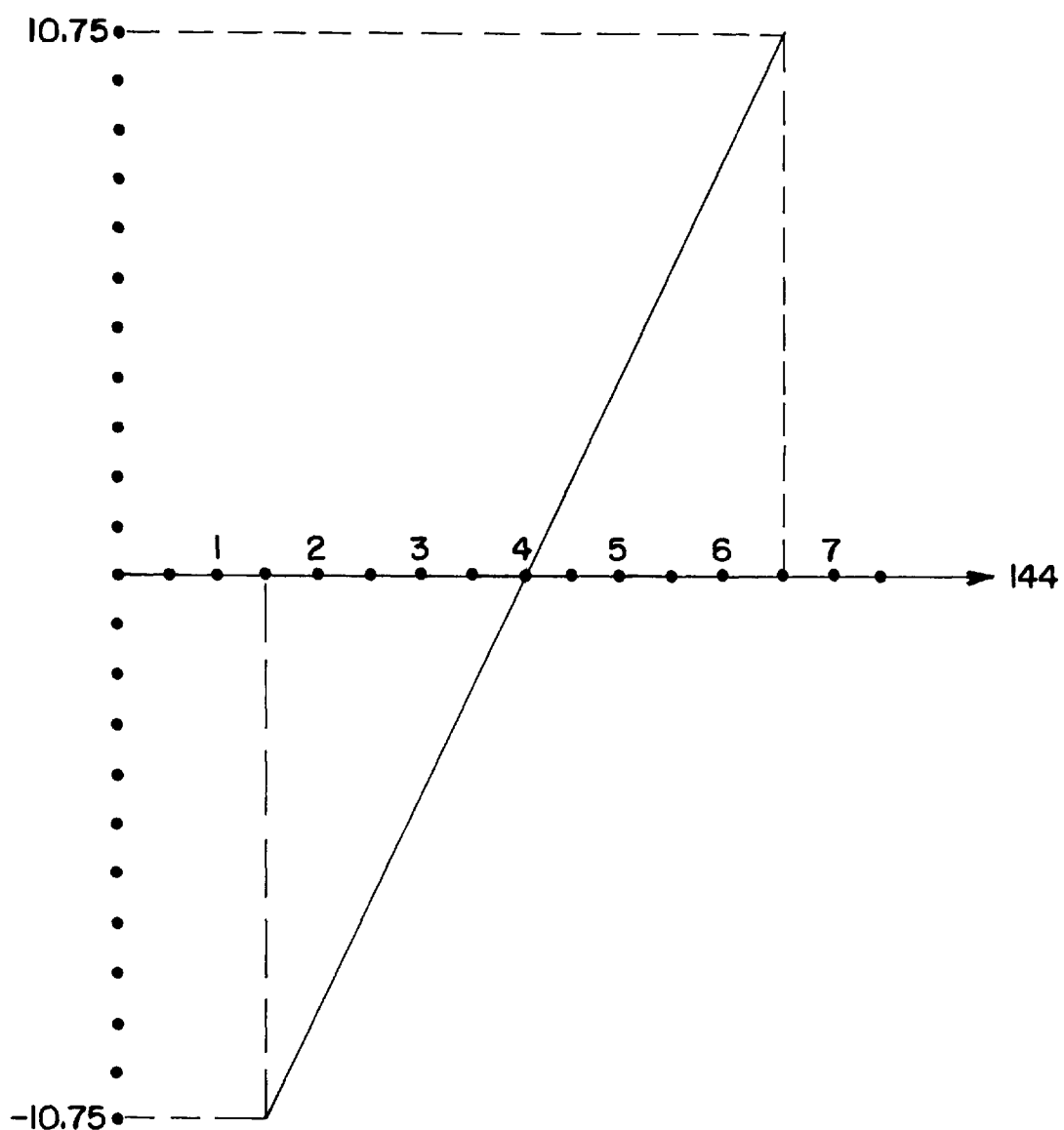
FIG. 12 is a graph showing the input signal voltage level versus the net voltage applied to the motor for the motor driver shown in FIG. 11.

In operation, the motor driver 104 responds to the input signal 144 as shown in FIG. 12, which is a graph of the input signal 144 voltage level versus the net voltage applied to the motor 64 for the motor driver 104 shown in FIG. 11. The net voltage applied to the motor 64 is the difference between the output of the power operational amplifier 150 and the output of the power operational amplifier 148.

When the input signal 144 is 4.0 volts, the outputs of the power operational amplifiers 148 and 150 are the same, 5.78 volts. Because the positive and negative terminals of the motor 64 are at the same voltage, the net voltage applied to the motor 64 is zero and the motor 64 does not rotate. As the voltage of the input signal 144 increases from 4.0 volts, the output of the power operational amplifier 150 increases from 5.78 volts and the output of the power operational amplifier 148 decreases from 5.78 volts. The net positive voltage causes the motor 64 to rotate in the forward direction at a speed proportional to the net voltage. Similarly, as the voltage of the input signal 144 decreases from 4.0 volts, the output of the power operational amplifier 150 decreases from 5.78 volts and the output of the power operational amplifier 148 increases from 5.78 volts. The net negative voltage causes the motor 64 to rotate in the reverse direction at a speed proportional to the net voltage.

For the motor driver 104 shown in FIG. 11, the net voltage applied to the motor 64 is 4.3 times the difference between the input signal 144 and 4.0 volts. A linear change in the signal 144 produces a linear change in the net voltage applied to the motor 64. The power operational amplifiers 148 and 150 may be operated from an 11.5 volt source so that 5.78 volts is the approximate midpoint of the operational voltage range.

Figure 13:
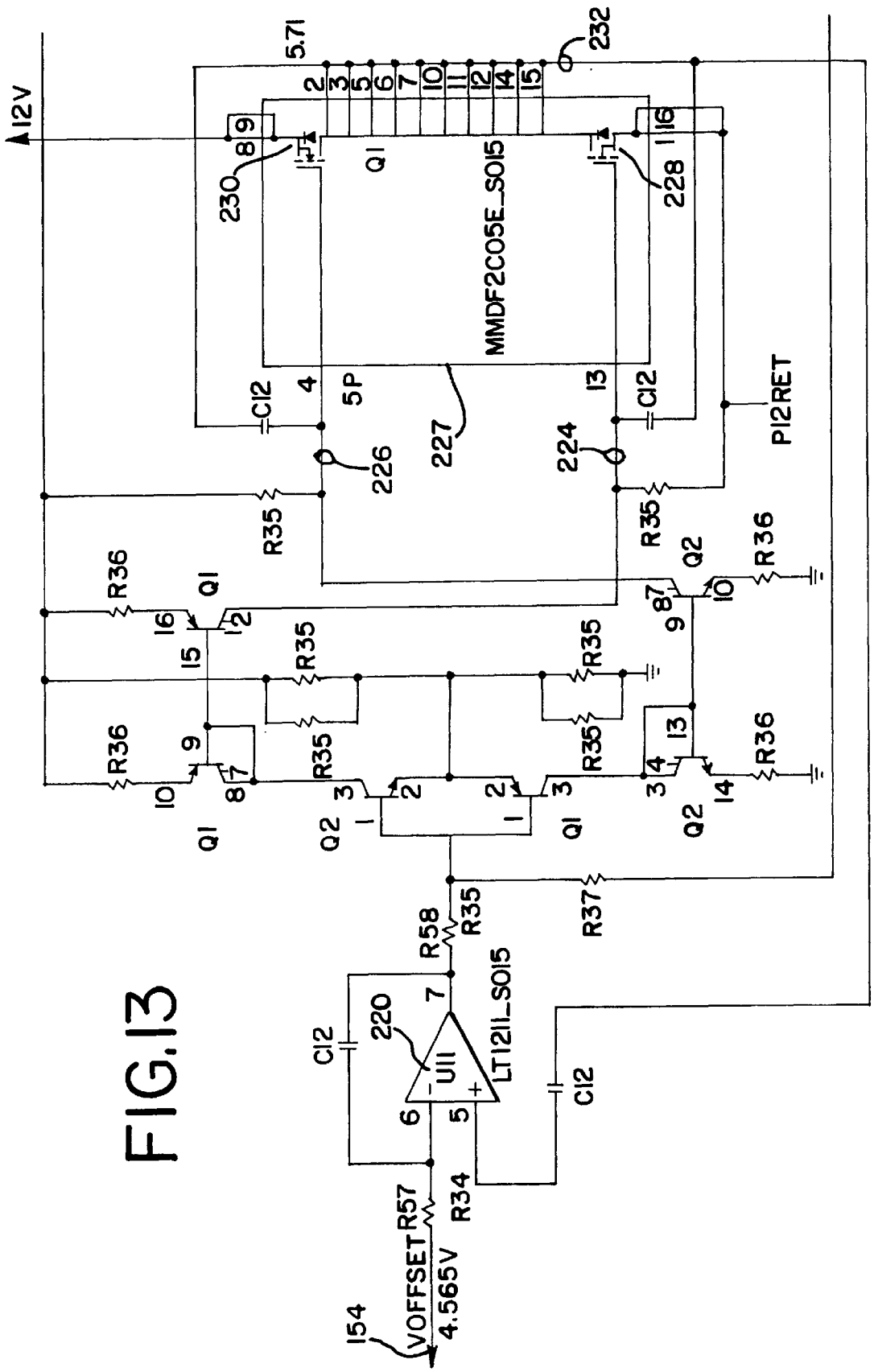
FIG. 13 is an electrical schematic of a power operational amplifier from the motor driver shown in FIG. 11.

FIG. 13 is an electrical schematic of the power operational amplifiers 148 and 150 shown in FIG. 11. The 4.565 volt reference 154 is coupled through a resistor R34 to the inverting input of an operational amplifier 220. The output of the operational amplifier 220 is coupled by a resistor R35 to a transistor driver stage 222. The transistor driver stage 222 supplies gate driver signals 224 and 226 to a power stage 227 containing a pair of MOSFETs 228 and 230, respectively. The output 232 of the power operational amplifier 148 is coupled to the negative terminal of the motor 64, whereas, for the power operational amplifier 150, the output 232 is coupled to the positive terminal of the motor 64. Component values for the electrical schematic of FIG. 13 are provided in Table 5 below. The operational amplifier 220 is preferably Part No. LT1211CS8 from Linear Technology of Milpitas, Calif.

The power stage 227 is preferably Part No. SI9950DY from Siliconix in Santa Clara, Calif., in which the MOSFET 230 is a p-channel device and the MOSFET 228 is an n-channel device. The transistors Q1 in FIG. 13 are PNP bipolar junction transistors, such as Part No. MMBT2907A manufactured by Motorola of Phoenix, Ariz. The transistors Q2 are NPN bipolar junction transistors, such as Part No. MMBT2222A, also manufactured by Motorola.

TABLE 5

| |
|---|
| R34 = 10.0 kΩ, 1%, THK |
| R35 = 1 kΩ, 1%, THK |
| R36 = 100 Ω, 1%, THK |
| R37 = 4.99 kΩ, .1%, THN |
| C12 = 1.0 nF COG 1% 50 v |

The amplifier/limiter 51, shown in FIG. 4, is preferably located on a printed circuit board within the control housing 12. The other circuitry described above is preferably located on printed circuit boards within the connector 22.

In a preferred embodiment of the invention, the ultrasound probe 10 may be operated in either a manual mode or a remote mode. When operated in the manual mode, the motor disable circuit 180 supplies the output of the gain block 60 as the desired velocity signal 188 to the velocity servo 102, unless the deadband detector 54 indicates that the control device 28 is positioned within the ±14% deadband. If, in the manual mode, the deadband detector 54 indicates that the control device 28 is positioned within the ±14% deadband, then the desired velocity signal 188 is forced to 4.0 volts (motor off), and the motor 64 is turned off.

When operated in the remote mode, the microprocessor 184 provides the FPGA 118 with information, such as when it should stop the motor 64 or change its speed. In addition, by communicating with the motor disable circuit 180, the microprocessor 184 is capable of starting motor 64 movement at a predetermined speed and direction. After being started by the microprocessor 184, motor control falls to the FPGA 118 and the microprocessor 184 preferably is turned off. It is the combination of the microprocessor 184 and the FPGA 118 that allows interference-free imaging in the remote mode.

Although the control device 28 is described herein with reference to manually controlling rotation of the ultrasound transducer 18, the control device 28 may be used in numerous other applications calling for a compact, manual bi-directional control device. For example, it may be used on construction equipment to control hydraulic pressure, on consumer electronics, including remote controls and scanning controls for televisions, stereos, video games and the like, and on machine tools and industrial equipment for hand-held power tool speed control, XYZ table/robotic manual controls and the like.

It is intended that the foregoing detailed description be regarded as illustrative rather than limiting, and it is understood that the following claims, including all equivalents, are intended to define the scope of the invention.

We claim:

1. A control device in an ultrasound transducer probe, comprising:
    a pivot bracket;
    a control button mounted to pivot about the pivot bracket;
    means for generating a magnetic field including a first magnetic field generator and a second magnetic field generator, the first magnetic field generator and the second magnetic field generator having substantially coplanar faces and opposite polarities, the generating means being attached to the control button; and
    means for sensing the magnetic field, the sensing means being located in a position adjacent the pivot bracket and wherein the sensing means provides a continuously variable output signal dependent upon the positioning of the control button.

2. A control device as claimed in claim 1, wherein the first and second magnetic field generators comprise first and second magnets.

3. A control device as claimed in claim 1, further comprising a mounting structure, wherein the mounting structure fixes the position of the sensing means in relation to the control button.

4. A control device as claimed in claim 1, wherein the sensing means comprises a hall-effect sensor.

5. A control device as claimed in claim 1, wherein the pivot bracket comprises a pivot pin that is formed from a ferromagnetic material.

6. A control device as claimed in claim 1, wherein the sensing means is fastened to the pivot bracket.

7. A control device as claimed in claim 1, wherein the sensing means may be adjustably positioned in relation to the generating means.

8. A control device as claimed in claim 5, further comprising a shim located between the pivot pin and the generating means.

9. A control device as claimed in claim 1, further comprising at least one return spring positioned between the control button and the pivot bracket.

10. A control device as claimed in claim 8, wherein a pivot pin formed from a ferromagnetic material is attached to the pivot bracket, and the control button pivots about the pivot pin.

11. A control device as claimed in claim 8, wherein the pivot pin has a flat surface which defines a neutral position.

12. A control device as claimed in claim 4, further comprising an electrical power supply coupled to the hall-effect sensor.

13. A control device as claimed in claim 12, wherein the electrical power supply comprises a direct current source.

14. A control device as claimed in claim 12, wherein the hall-effect sensor provides an output signal having a predetermined amplitude corresponding to a position of the control button.

15. A control device for converting a manual input into an electrical signal in an ultrasound transducer probe, comprising:
    a control button mounted for pivotal displacement about a neutral position in accordance with the manual input;
    a first magnet having a first predetermined polar orientation, the first magnet being mounted to the control button;
    a second magnet having a second predetermined polar orientation, wherein the polar orientation of the second magnet is opposite the polar orientation of the first magnet, the second magnet being mounted to the control button; the first magnet and the second magnet having substantially coplanar faces and
    a hall-effect sensor located adjacent to the control button, the hall-effect sensor having an electrical input and a continuously variable electrical output dependent upon the positioning of the control button.

16. A control device as claimed in claim 15, wherein the electrical output comprises a direct current signal having an amplitude corresponding to the pivotal displacement of the control button.

17. A control device for a transducer in an ultrasound transducer probe, comprising:
    a magnetic field generator;
    a magnetic field sensor positioned adjacent the generator;
    a control button affecting the magnetic field sensed by the magnetic field sensor in response to movement of the control button; and
    said transducer capable of being positioned at continuously variable speeds in response to the magnetic field sensed by the magnetic field sensor.

18. A control device for a transducer as claimed in claim 17, wherein the magnetic field generator comprises a first magnet and a second magnet, the first magnet being oriented to have an opposite polarity than the second magnet.

19. A control device for a transducer as claimed in claim 17, further comprising a mounting structure, wherein the mounting structure fixes the position of the magnetic field sensor in relation to the control button.

20. A control device for a transducer as claimed in claim 17, wherein the magnetic field sensor comprises a hall-effect sensor.

21. A control device for a transducer as claimed in claim 17, further comprising a pivot bracket having a pivot pin formed from a ferromagnetic material, the control button being pivotable with respect to the pivot pin.

22. A control device for a transducer as claimed in claim 21, wherein the magnetic field sensor is fastened to the pivot bracket.

23. A control device for a transducer as claimed in claim 22, wherein the magnetic field sensor is adjustably mounted in relation to the magnetic field generator.

24. A control device for a transducer as claimed in claim 21, further comprising a shim located between the pivot pin and the magnetic field generator.

25. A control device for a transducer as claimed in claim 17, further comprising at least one return spring positioned between the control button and a pivot bracket.

26. A control device for a transducer as claimed in claim 25, wherein a pivot pin formed from a ferromagnetic material is attached to the pivot bracket, and the control button pivots about the pivot pin.

27. A control device for a transducer as claimed in claim 26, wherein the pivot pin has a flat surface which defines a neutral position.

28. A control device for a transducer as claimed in claim 20, further comprising an electrical power supply coupled to the hall-effect sensor.

29. A control device for a transducer as claimed in claim 28, wherein the electrical power supply comprises a direct current source.

30. A control device for a transducer as claimed in claim 29, wherein the hall-effect sensor provides an output signal having a predetermined amplitude corresponding to a position of the control button.

* * * * *